US006765100B2

(12) United States Patent
Onishi et al.

(10) Patent No.: US 6,765,100 B2
(45) Date of Patent: Jul. 20, 2004

(54) METHOD FOR PRODUCING EPOXIDE CRYSTAL

(75) Inventors: Tomoyuki Onishi, Kawasaki (JP);
Naoko Hirose, Kawasaki (JP);
Yasuyuki Otake, Kawasaki (JP);
Takashi Nakano, Kawasaki (JP);
Yutaka Honda, Kawasaki (JP);
Masakazu Nakazawa, Kawasaki (JP);
Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/973,191

(22) Filed: Oct. 10, 2001

(65) Prior Publication Data

US 2002/0072621 A1 Jun. 13, 2002

Related U.S. Application Data

(63) Continuation of application No. 09/652,679, filed on Aug. 31, 2000, now abandoned.

(30) Foreign Application Priority Data

Aug. 31, 1999 (JP) ............................................ 11-245645
Feb. 14, 2000 (JP) ....................................... 2000-035074
Mar. 23, 2000 (JP) ....................................... 2000-082895
Jun. 30, 2000 (JP) ....................................... 2000-199234

(51) Int. Cl.$^7$ .................... C07D 301/24; C07D 263/38; C07C 271/00
(52) U.S. Cl. ....................... 549/520; 549/521; 548/230; 560/160
(58) Field of Search .................. 560/160; 549/520, 549/521; 548/230

(56) References Cited

U.S. PATENT DOCUMENTS 5,481,011 A    1/1996  Chen et al.
5,559,256 A    9/1996  Gordon et al.

FOREIGN PATENT DOCUMENTS

| EP | 0 532 466    | 3/1993  |
| EP | 0 754 669    | 1/1997  |
| EP | 0 774 453    | 5/1997  |
| EP | 1 050 532 A2 | 11/2000 |
| EP | 1 052 257 A1 | 11/2000 |
| EP | 1 067 125    | 1/2001  |
| EP | 1 151 992    | 11/2001 |
| WO | WO 92/08700  | 5/1992  |
| WO | WO 96/23756  | 8/1996  |
| WO | WO 00/43357  | 7/2000  |
| WO | WO 00/44736  | 8/2000  |

OTHER PUBLICATIONS

P. Raddatz, et al, J. Med. Chem., vol. 34, pps. 3267–3280, "Substrate Analogue Renin Inhibitors Containing Replacements of Histidine in P$_2$ or Isosteres of the Amide Bond Between P$_3$ and P$_2$ Sites," 1991.

S. Romeo, et al., Tetrahedron Letters, vol. 35, No. 28, pps. 4939–4942, "Stereoselective Synthesis of Protected Amino Alkyl Epoxides," 1994.

T. Archibald, et al., Scientific Update Conference Manual, pp. 1–10 and drawing pp. 1–5, "Full Scale Chiral Separations using SMB," May 4, 1999.

S.H. Kang, et al., Bioorganic & Medical Chemistry Letters, vol. 5, No. 24, , pps. 2959–2962, "Versatile Synthetic Routes to Threo–β–Amino Hydroxy Carboxylic Acids, Statine and its Analogues", 1995.

L. Pégorier, et al., Tetrahedron Letters, vol. 36, No. 16, pps 2753–2756, "A General Stereocontrolled Synthesis of Hydroxyethylene Dipeptide Isosteres," 1995.

P. Chen, et al., Tetrahedron Letters, vol. 38, No. 18, pps. 3175–3178, "A Practical Method for the Preparation of α'–Chloroketones of N–Carbamate Protected–α–Aminoacids," 1997.

A. Albeck, et al., Tetrahedron Letters, vol. 50, No. 21, pps. 6333–6346, "Stereocontrolled Synthesis of Erythro N–Protected A–Amino Epoxides and Peptidyl Epoxides," 1994.

Evans et al Journal of Organic Chemistry 1985, 50(23) pp. 4615–4625.

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

The invention relates to a method for industrially producing highly pure (2R, 3S)- or (2S, 3R)-N-carbamate-protected β-aminoepoxide (crystal) or (2R, 3S)- or (2S, 3R)-N-carbamate-protected β-aminoalcohol. The method for producing N-carbamate-protected β-aminoepoxide crystal, includes one or more of the following steps (a) to (d):

(a) dissolving (2R, 3S)- or (2S, 3R)-N-carbamate-protected β-aminoalcohol containing at least the diastereomer as an impurity in a solvent including at least one or more selected from aromatic hydrocarbon solvent, saturated hydrocarbon solvent, aqueous mixture solvent, acetone and 2-propanol, to remove insoluble matters;

(b) treating the (2R, 3S)- or (2S, 3R)-N-carbamate-protected β-aminoalcohol with a base, thereby converting the N-carbamate-protected β-aminoalcohol to (2R, 3S)- or (2S, 3R)-N-carbamate-protected β-aminoepoxide;

(c) treating the (2R, 3S)- or (2S, 3R)-N-carbamate-protected β-aminoepoxide containing at least the diastereomer as an impurity with an acid, thereby converting the diastereomer as an impurity to (4S, 5R) or (4R, 5S) oxazolidin-2-one derivative, and optionally separating and removing the resulting oxazolidin-2-one derivative in water or an aqueous mixture solvent; and (d) crystallizing the (2R, 3S)- or (2S, 3R)-N-carbamate-protected β-aminoepoxide in a mixture solvent of water and water-miscible organic solvent. By the methods of the present invention, highly pure (2R, 3S)- or (2S, 3R)-N-carbamate-protected β-aminoepoxide or (2R, 3S) or (2S, 3R)-N-carbamate-protected β-aminoalcohol can be efficiently produced.

57 Claims, No Drawings

METHOD FOR PRODUCING EPOXIDE CRYSTAL

This application is a continuation of 09/652,679 filed Aug. 31, 2000 now abandoned.

FIELD OF THE INVENTION

The present invention relates to a method for producing and purifying N-carbamate-protected β-aminoepoxide with a specific steric configuration {(2R, 3S) or (2S, 3R)} and a method for producing the crystal. The invention also relates to a method for producing and purifying N-carbamate-protected β-aminoalcohol with a specific steric configuration {(2R, 3S) or (2S, 3R)}.

BACKGROUND OF THE INVENTION

The N-carbamate-protected β-aminoepoxide represented by the general formula (2) is a useful compound as a pharmaceutical intermediate:

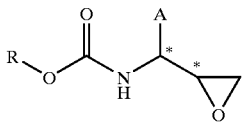

(2)

{in the formula, R represents a lower alkyl group, benzyl group or fluorenylmethyl group; A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing a hetero atom in these carbon backbones; * represents asymmetric carbon atom; the steric configuration at 2- and 3-positions is (2R, 3S) or (2S, 3R)}.

It is known for example that (2R, 3S)-N-carbamate-protected β-aminoepoxide is useful as an intermediate of HIV protease inhibitors and renin inhibitors (see for example Raddatz et al., Journal of Medicinal Chemistry, 1991, 34, 11,3269 or T. Archibald et al., Scientific Update Conference Manual, Chiral USA 99, Full Scale Chiral Separations Using SMB, May 4, 1999, San Francisco, Scientific Update).

It has been known that N-carbamate-protected β-aminoepoxide represented by the general formula (2) can be synthesized according to the following pathway.

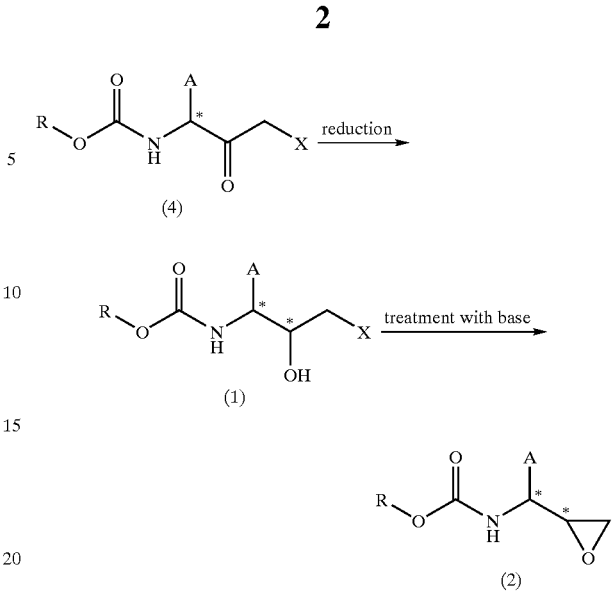

{in the formula, R and A represent the same meanings described above; X represents halogen atom}.

When (3S)-N-carbamate-protected α-halomethylketone as the compound represented by the general formula (4) is used as a starting material, for example, the starting material is reduced to afford (2R, 3S)-N-carbamate-protected β-aminoalcohol, followed by treatment with a base, to afford (2R, 3S)-N-carbamate-protected β-aminoepoxide.

Similarly, when (3R)-N-carbamate-protected α-halomethylketone is used as a starting material, the starting material is reduced to afford (2S, 3R)-N-carbamate-protected β-aminoalcohol, followed by treatment with a base, to afford (2S, 3R)-N-carbamate-protected aminoepoxide.

Herein, the reduction of N-carbamate-protected α-halomethylketone with an appropriate reducing agent involves the generation of the diastereomer as a byproduct.

For example, the reduction of (3S)-N-carbamate-protected α-halomethylketone represented by the general formula (13) involves the generation of the diastereomer (2S, 3S)-N-carbamate-protected β-aminoalcohol (7) as a byproduct.

Upon treatment with a base, the byproduct is converted to as (2S, 3S)-N-carbamate-protected β-aminoepoxide (11) as the diastereomer of the objective compound (see the following scheme).

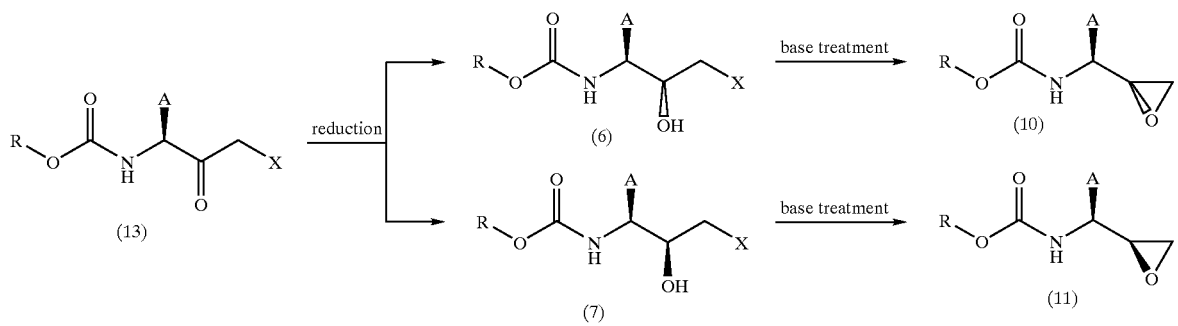

{in the formulas, R, A, X represent the same meanings as described above.}

More specifically, for example, it is reported that the reduction of, e.g., (3S)-3-tert-butoxycarbonylamino-1-halo-4-phenyl-2-butane in ether with lithium aluminum tri-tert-butoxyhydride involves the generation of the diastereomer (2S, 3S)-3-tert-butoxycarbonylamino-1-halo-2-hydroxy-4phenylbutane at a ratio of about 1 mol equivalent to 5 to 8 mol equivalents of the objective (2R, 3S) compound (see P. Raddatz et al., J. Med. Chem., 1991, 34, 11, 3269 or T. Archibald et al., Scientific Update Conference Manual, Chiral USA 99, Full Scale Chiral Separations Using SMB, May 4, 1999, San Francisco, Scientific Update). (2R, 3S)-3-tert-butoxycarbonylamino 1,2-epoxy-4-phenylbutane afforded by an additional treatment with a base also contains the diastereomer at about the same ratio.

The above references disclose methods for separating (2R, 3S)-N-carbamate-protected β-aminoalcohol or (2R, 3S)-N-carbamate-protected β-aminoepoxide by silica gel chromatography or high-performance liquid chromatography, but the methods require the use of vast amounts of expensive carriers and solvents and take a long time due to the complex procedures. Accordingly, these methods are not industrially appropriate.

Of the references above, the latter reference discloses on page 3 that because (2R, 3S)-N-carbamate-protected β-aminoalcohol or (2R, 3S)N-carbamate-protected β-aminoepoxide is at a lower melting point and a higher solubility than those of the diastereomer, the ratio of the diastereomer to the objective compound can be reduced to 94:6, at most, by purification with crystallization and that no more purification thereof by recrystallization is possible.

Further, the technique for removing other impurities is not necessarily satisfactory. Hence, the development of an industrial method for producing highly pure (2R, 3S)- or (2S, 3R)-N-carbamate-protected β-aminoepoxide has been desired.

BRIEF SUMMARY OF THE INVENTION

It is an object of the present invention to provide an industrial method for producing (2R, 3S)- or (2S, 3R)-N-carbamate-protected β-aminoepoxide (including the crystal) and N-carbamate-protected β-aminoalcohol.

The present inventors have made investigations so as to solve the problem. The following findings have been found.

1) By dissolving (2R, 3S)-N-carbamate-protected β-aminoalcohol containing at least the diastereomer as an impurity or an optical isomer thereof in a solvent including at least one or more selected from aromatic hydrocarbon solvent, aryl halide solvent, saturated hydrocarbon solvent, aqueous mixture solvent, acetone and 2-propanol, thereby removing insoluble matters, the diastereomer as an impurity is highly separated and removed.

2) By treating (2R, 3S)-N-carbamate-protected β-aminoepoxide containing at least the diastereomer as an impurity or an optical isomer thereof with an acid, thereby converting the diastereomer as an impurity to oxazolidin-2-one derivative, and separating and removing the resulting derivative in water or an aqueous mixture solvent, the diastereomer as an impurity is highly separated and removed.

3) By crystallizing (2R, 3S)-N-carbamate-protected β-aminoepoxide or an optical isomer thereof in an aqueous mixture solvent, a more highly pure crystal of the epoxide can be obtained.

Accordingly, the object of the present invention, and others, may be accomplished with a method for producing N-carbamate-protected β-aminoepoxide crystal including:

(a) dissolving N-carbamate-protected β-aminoalcohol containing at least the diastereomer as an impurity and being represented by the general formula (1), in a solvent including at least one or more selected from aromatic hydrocarbon solvent, saturated hydrocarbon solvent, aqueous mixture solvent, acetone and 2-propanol, to remove insoluble matters:

(1)

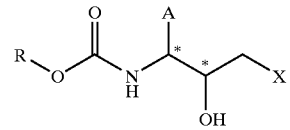

{in the formula, R represents a lower alkyl group, benzyl group or fluorenylmethyl group; A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in these carbon backbones; X represents halogen atom; * represents asymmetric carbon atom; the steric configuration at 2- and 3-positions is (2R, 3S) or (2S, 3R)};

(b) treating the N-carbamate-protected β-aminoalcohol represented by the general formula (1) with a base, thereby converting the N-carbamate-protected β-aminoalcohol to N-carbamate-protected β-aminoepoxide represented by the general formula (2):

(2)

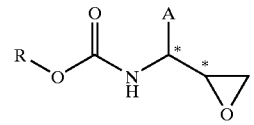

{in the formula, R, A and * represent the same meanings as described above; the steric configuration at 2- and 3-positions is (2R, 3S) or (2S, 3R)};

(c) treating the N-carbamate-protected β-aminoepoxide containing at least the diastereomer as an impurity and being represented by the general formula (2) with an acid, thereby converting the diastereomer as an impurity to oxazolidin-2-one derivative represented by the general formula (3):

(2)

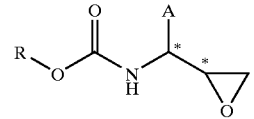

{in the formula, R represents a lower alkyl group, benzyl group or fluorenylmethyl group; A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in these carbon backbones; * represents asymmetric carbon atom; the steric configuration at 2- and 3-positions is (2R, 3S) or (2S, 3R)

(3)

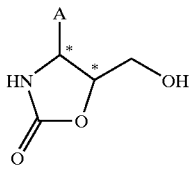

{in the formula, A and * represent the same meaning as described above; the steric configuration at 4- and 5-positions is (4S, 5R) or (4R, 5S)}, and, if necessary, separating and removing the resulting oxazolidin-2-one derivative in water or an aqueous mixture solvent; and (d) crystallizing the N-carbamate-protected aminoepoxide represented by the general formula (2) in an aqueous mixture solvent.

Another embodiment of the invention provides a crystal of N-carbamate-protected β-aminoepoxide represented by the formula (2), which is produced by the above method.

Another embodiment of the invention provides a method for producing an N-carbamate-protected β-aminoalcohol, which includes:

(a) dissolving N-carbamate-protected β-aminoalcohol including at least a diastereomer thereof as an impurity and represented by the formula (1) in at least one solvent selected from the group including aromatic hydrocarbon, aryl halide, saturated hydrocarbon, aqueous mixture, acetone and 2-propanol, to remove insoluble materials:

(1)

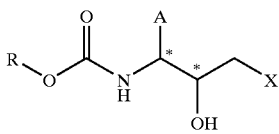

wherein in formula (1):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone;
X represents halogen atom; and
* represents asymmetric carbon atom;
wherein the steric configuration at 2- and 3-positions is (2R, 3S) or (2S, 3R).

Another embodiment of the present invention provides a method for producing an N-carbamate-protected β-aminoepoxide, which includes:

(a) dissolving N-carbamate-protected β-aminoalcohol including at least a diastereomer thereof as an impurity and represented by the formula (1), in at least one solvent selected from the group including aromatic hydrocarbon, aryl halide, saturated hydrocarbon, aqueous mixture solvent, acetone and 2-propanol, to remove insoluble materials:

(1)

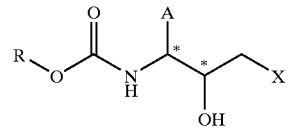

wherein in formula (1):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone;
X represents halogen atom; and
* represents asymmetric carbon atom;
wherein the steric configuration at 2- and 3-positions is (2R, 3S) or (2S, 3R);

(b) treating the N-carbamate-protected β-aminoalcohol represented by the formula (1) with a base, thereby converting the N-carbamate-protected β-aminoalcohol to N-carbamate-protected β-aminoepoxide represented by the formula (2):

(2)

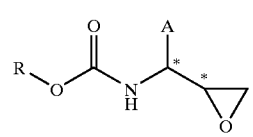

wherein in formula (2), R, A and * have the same meanings as recited above; and wherein the steric configuration at 2- and 3-positions is (2R, 3S) or (2S, 3R).

Another embodiment of the present invention provides a method for producing an N-carbamate-protected β-aminoepoxide crystal, which includes:

(c) treating the N-carbamate-protected β-aminoepoxide including at least a diastereomer thereof as an impurity and represented by the formula (2) with an acid, thereby converting the diastereomer to oxazolidin-2-one derivative represented by the formula (3):

(2)

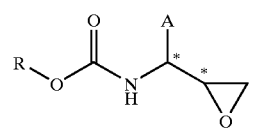

wherein in formula (2):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone; and
* represents asymmetric carbon atom; and wherein the steric configuration at 2- and 3-positions is (2R, 3S) or (2S, 3R);

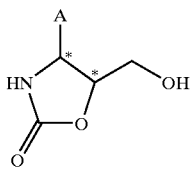
(3)

wherein in formula (3), A and * have the same meaning as recited above; and wherein the steric configuration at 4- and 5-positions is (4S, 5R) or (4R, 5S), and optionally separating and removing the resulting oxazolidin-2-one derivative in water or an aqueous mixture solvent; and (d) crystallizing the N-carbamate-protected aminoepoxide represented by the formula (2) in an aqueous mixture solvent.

Another embodiment of the present invention provides a crystal of the N-carbamate-protected β-aminoepoxide represented by the formula (2), which is produced by the above method.

Another embodiment of the present invention provides a method for producing an N-carbamate-protected β-aminoepoxide crystal, which includes:

(d) crystallizing the N-carbamate-protected β-aminoepoxide represented by the formula (2) in an aqueous mixture solvent:

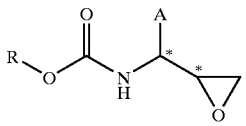
(2)

wherein in formula (2):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone; and
* represents asymmetric carbon atom; the steric configuration at 2- and 3-positions is (2R, 3S) or (2S, 3R).

Another embodiment of the present invention provides a crystal of N-carbamate-protected β-aminoepoxide represented by the formula (2), which is produced by the above method.

Another embodiment of the present invention provides a method for producing an N-carbamate-protected aminoepoxide, which includes:

(c) treating the N-carbamate-protected aminoepoxide including at least a diastereomer thereof as an impurity and being represented by the formula (2) with a solid acid insoluble in solvents, thereby converting the diastereomer to oxazolidin-2-one derivative represented by the formula (3):

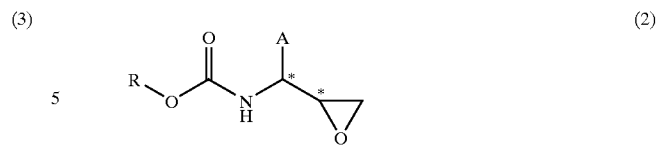
(2)

wherein in formula (2):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone; and
* represents asymmetric carbon atom; wherein the steric configuration at 2- and 3-positions is (2R, 3S) or (2S, 3R);

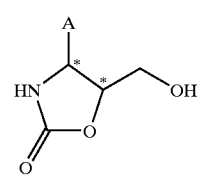
(3)

wherein in formula (3), A and * have the same meaning as recited above; and wherein the steric configuration at 4- and 5-positions is (4S, 5R) or (4R, 5S); and separating and removing the resulting oxazolidin-2-one derivative in water or an aqueous mixture solvent.

By the methods of the present invention, highly pure (2R, 3S)- or (2S, 3R)-N-carbamate-protected β-aminoepoxide or (2R, 3S) or (2S, 3R)-N-carbamate-protected β-aminoalcohol can be efficiently produced.

DETAILED DESCRIPTION OF THE INVENTION

Various other objects, features and attendant advantages of the present invention will be more fully appreciated as the same becomes better understood from the following detailed description of the preferred embodiments of the invention.

In the present specification, (2R, 3S)-N-carbamate-protected β-aminoalcohol is sometimes abbreviated as (2R, 3S) alcohol; and the diastereomer as an impurity is sometimes abbreviated as (2S, 3S) alcohol.

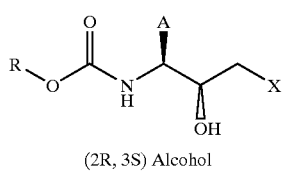
(5)
(2R, 3S) Alcohol

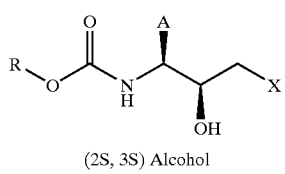
(6)
(2S, 3S) Alcohol

Additionally, (2S, 3R)-N-carbamate-protected β-aminoalcohol is sometimes abbreviated as (2S, 3R) alcohol; and the diastereomer as an impurity is sometimes abbreviated as (2R, 3R) alcohol.

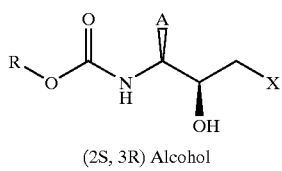

(2S, 3R) Alcohol (7)

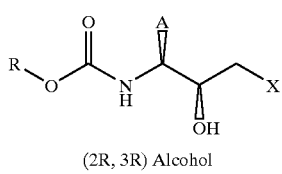

(2R, 3R) Alcohol (8)

Still additionally, (2R, 3S)-N-carbamate-protected β-aminoepoxide is sometimes abbreviated as (2R, 3S) epoxide; and the diastereomer as an impurity is sometimes abbreviated as (2S, 3S) epoxide.

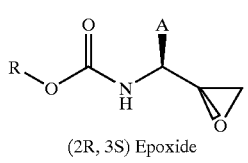

(2R, 3S) Epoxide (9)

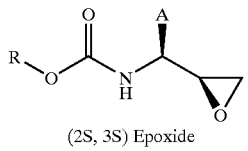

(2S, 3S) Epoxide (10)

Furthermore, (2S, 3R)-N-carbamate-protected β-aminoepoxide is sometimes abbreviated as (2S, 3R) epoxide; and the diastereomer as an impurity is sometimes abbreviated as (2R, 3R) epoxide.

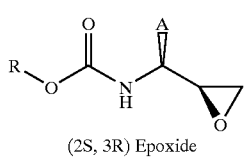

(2S, 3R) Epoxide (11)

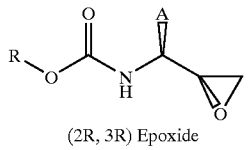

(2R, 3R) Epoxide (12)

In the formulas in accordance with the invention, X represents halogen atom. As the halogen atom, chlorine atom and bromine atom are preferable; and chlorine atom is particularly preferable.

In the formulas in accordance with the invention, R represents a lower alkyl group, benzyl group or fluorenylmethyl group. As the R, a lower alkyl group is preferable. The lower alkyl group includes an alkyl group with 1 to 8 carbon atoms, preferably an alkyl group with 1 to 4 carbon atoms. Methyl group, ethyl group and tert-butyl group are particularly preferred.

As the R, tert-butyl group is most particularly preferable.

In the formulas in accordance with the invention, A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing a hetero atom in these carbon backbones. Preferably, A represents an unsubstituted or substituted alkyl group with 1 to 8 carbon atoms, an unsubstituted or substituted aryl group with 6 to 13 carbon atoms or an unsubstituted or substituted aralkyl group with 7 to 18 carbon atoms, or a group containing a hetero atom in these carbon backbones. When A is substituted one or more groups as abovementioned, the substituent is not particularly limited unless it especially affect the reaction of the invention. The substituent includes, for example, alkoxyl group (preferably with 1 to 7 carbon atoms), nitro group, alkyl group (preferably with 1 to 6 carbon atoms), and halogen atom.

The group containing one or more hetero atoms in these carbon backbones includes, for example, methylthioethyl group, t-butylthiomethyl group, tritylthiomethyl group, (p-methylbenzyl)thiomethyl group, (p-methoxybenzyl)thiomethyl group, t-butoxymethyl group, benzyloxymethyl group, t-butoxyethyl group, benzyloxyethyl group, 4-(t-butoxy)phenylmethyl group, 4-benzyloxyphenylmethyl group and phenylthiomethyl group.

Such groups can be introduced by using for example amino acid as a raw material. In case that A is methyl group, for example, alanine is used as a raw material; in case that A is isopropyl group, valine is used as a raw material; in case that A is 2-methylpropyl group, leucine is used as a raw material; in case that A is 1-methylpropyl group, isoleucine is used as a raw material; in case that A is benzyl group, phenylalanine is used as a raw material; in case that A is methylthioethyl group, methionine is used as a raw material.

Additionally, A may satisfactorily be a group introduced from a raw material amino acid with a functional group in the side chain of the amino acid under protection, for example S-t-butylcysteine, S-tritylcysteine, S-(p-methylbenzyl)cysteine, S-(p-methoxybenzyl)cysteine, O-t-butylserine, O-benzylserine, O-t-butylthreonine, O-benzylthreonine, O-t-butyltyrosine and O-benzyltyrosine.

Furthermore, A is not limited to groups introduced from raw materials derived from natural amino acid, but may satisfactorily be groups (for example, phenyl group and phenylthiomethyl group) introduced from raw materials derived from non-natural amino acid.

In accordance with the invention, preference is given to compounds wherein A is an aryl group with 6 to 15 carbon atoms, an aralkyl group with 7 to 20 carbon atoms or a group containing a hetero-atom in these carbon backbones; furthermore, preference is given to compounds wherein A is an aralkyl group with 7 to 20 carbon atoms or a group containing a hetero-atom in these carbon backbones. More specifically, preference is given to compounds wherein A is benzyl group, phenylthiomethyl group, 4-benzyloxyphenylmethyl group, isopropyl group, 2-methylpropyl group and 1-methylpropyl group; still furthermore, preference is given to compounds wherein A is benzyl group, phenylthiomethyl group and 4-benzyloxyphenylmethyl group. Compounds wherein A is benzyl group are particularly preferable.

The preferable process (a) is described below.

N-Carbamate-protected β-aminoalcohol containing at least the diastereomer as an impurity and being represented by the general formula (1), namely the (2R, 3S) alcohol or (2S, 3R) alcohol, may be obtained by reducing (3S)-N-carbamate protected α-aminohalomethylketone represented by the general formula (13) or (3R)-N-carbamate-protected aminohalomethylketone represented by the general formula (14)

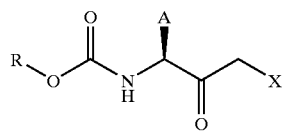

(13)

{in the formula, R, A and X represent the same meanings as described above}

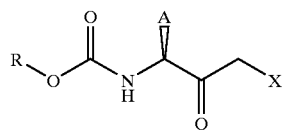

(14)

{in the formula, R, A and X represent the same meanings as described above}.

It has been known that the ratio of the generated (2R, 3S) alcohol and (2S, 3S) alcohol through reduction varies depending on the type of a reducing agent. By selecting an appropriate reducing agent, the ratio of the diastereomer as an impurity can be suppressed at some extent (see T. Archibald et al., Scientific Update Conference Manual, Chiral USA 99, Full Scale Chiral Separations Using SMB, May 4, 1999, San Francisco, Scientific Update). This is the same for the ratio of the (2S, 3R) alcohol and the (2R, 3R) alcohol in the case of the reduction of (3R)-N-carbamate-protected α-aminohalomethylketone.

Preferable reducing agents include for example lithium aluminum tri-tert-butoxyhydride, (+)-B-chlorodiisopinocamphenylborane, and boron potassium trisec-butylhydride; particularly, lithium aluminum tri-tert butoxyhydride is preferable.

Herein, (3S)-N-protected α-aminohalomethylketone and (3R)-N-protected α-aminohalomethylketone can be produced by known methods, for example, such as the method including allowing amino acid ester with the amino group under protection, to react with a metal enolate prepared from α-haloacetic acid, thereby eliminating carbonate (see International Patent Publication WO 96/23756).

When the reaction mixture recovered by the method is subjected for example to the process (a) of the invention, the ratio of the objective (2R, 3S) alcohol or (2S, 3R) alcohol is preferably high. Even when the ratio of each of these diastereomers to the (2R, 3S) alcohol or (2S, 3R) alcohol is high, the method of the invention is applicable.

The method of the invention is applicable to a mixture at a molar ratio of (2S, 3S) alcohol/(2S, 3R) alcohol or (2R, 3R) alcohol/(2S, 3R) alcohol, below 100, preferably below 1, more preferably below ½, particularly preferably below ⅓.

The aromatic hydrocarbon solvent to be used at the process (a) includes for example benzene, xylene, toluene and an appropriate mixture solvent of these solvents Particularly, xylene, toluene and an appropriate mixture solvent of these solvents are preferable; toluene is particularly preferable.

The aryl halide solvent to be used at the process (a) includes for example chlorobenzene, bromobenzene and appropriate mixture solvents of these solvents. Particularly, chlorobenzene is preferable.

The saturated hydrocarbon solvent to be used at the process (a) includes for example n-pentane, n-hexane, n-heptane, n-octane, n-nonane, n-decane, isohexane, isooctane, cyclopentane, cyclohexane, methylcyclohexane, petroleum ether, and appropriate mixture solvents of these solvents.

Particularly preferable solvents include n-hexane, n-heptane, cyclohexane, methylcyclohexane and appropriate mixtures of these solvents. Particularly, n-heptane is preferable.

The aqueous mixture solvent at the process (a) means a mixture solvent of a water-miscible organic solvent with water; the organic solvent miscible with water includes methanol, ethanol, 1-propanol, 2-propanol, acetone, 2-butanone, acetonitrile and tetrahydrofuran. Methanol, ethanol, 2-propanol, acetone and appropriate mixture solvents of these solvents are preferable; furthermore, methanol, ethanol, 2-propanol and appropriate mixture solvents of these solvents are more preferable; and particularly, 2-propanol is preferable. Acetone and 2-propanol can be used singly, but preferably, they are used in the form of mixture solvents with water.

The composition ratio of water and an organic solvent is not particularly limited, but the ratio is preferably 5 to 95%, more preferably 25 to 90% (% is expressed as the volume ratio of an organic solvent in a mixture solvent).

More preferable are aromatic hydrocarbon solvents and aqueous mixture solvents among the solvents for use at the process (a). Particularly, aromatic hydrocarbon solvents are preferable. Among them, more preferable are toluene, xylene and a mixture solvent of 2-propanol with water; particularly, toluene is preferable.

As far as the advantages of the invention are not adversely influenced, other solvents may be added to the solvent for use as the solvent at the process (a).

At the process (a) of the invention, the (2R, 3S) alcohol or (2S, 3R) alcohol at least containing the diastereomer as an impurity is dissolved in aromatic hydrocarbon solvent, aryl halide solvent, saturated hydrocarbon solvent, acetone, 2-propanol or aqueous mixture solvent, to remove insoluble matters. More specifically, a state such that the objective (2R, 3S) alcohol or (2S, 3R) alcohol is dissolved in these solvents while the diastereomer is present as insoluble matters, is to be realized, despite any procedure adopted.

For example, a solvent including at least one or more selected from aromatic hydrocarbon solvent, aryl halide solvent, saturated hydrocarbon solvent, aqueous mixture solvent, acetone and 2-propanol is added to the (2R, 3S) alcohol or (2S, 3R) alcohol at least containing the diastereomer as an impurity, for agitation. Then, the (2R, 3S) alcohol or (2S, 3R) alcohol is relatively readily dissolved in these solvents, while the diastereomer thereof is slightly soluble and turns insoluble matters to be generally prepared as a form of slurry, although the form depends on the content of impurities, the solvent volume and the temperature. For example, at a high temperature above ambient temperature, the slurry form is modified into a solution state, which is then cooled down to an appropriate temperature to deposit the diastereomer as an impurity.

For example, for subjecting the reaction mixture obtained by reduction to the process (a) of the present invention, the reaction solvent is preferably concentrated or more preferably sufficiently evaporated after the reduction is terminated; and subsequently, the aforementioned solvent is added to the resulting residue, from the respect of purification efficiency.

The quantity of solvent to be added is not particularly limited, but is preferably at a weight 1- to 50-fold the weight of a mixture to be subjected to the process (a). The temperature for agitation is not particularly limited and is for example a temperature at −20° C. to a temperature below the boiling point of the solvent to be used. The temperature preferably varies, depending on the type and quantity of the solvent to be used. So as to decrease the loss of the objective compound, for example, wherein a saturated hydrocarbon solvent is used, the solvent is heated to an appropriate temperature above ambient temperature and below the boiling point of the solvent (preferably, 35° C. to 70° C.), preferably, while insoluble matters are filtered under heating as they are. In case that an aromatic hydrocarbon solvent or aryl halide solvent is used, for example, the temperature of the solvent is controlled to below ambient temperature down to an appropriate temperature (for example, about −20° C.), preferably, while insoluble matters are filtered. In case that an aqueous mixture solvent is used, for example, insoluble matters are satisfactorily filtered within a range of about 0° C. to 50° C., which varies depending on the mixing ratio of water and a solvent. The agitation time is not particularly limited but is preferably 10 minutes to 6 hours; more preferably 30 minutes to 5 hours, and most preferably, 1 hour to 4 hours.

A person with an ordinary skill in the art can readily determine preferable conditions depending on the solvent to be used, on the basis of the description of the specification.

Then, insoluble matters are preferably removed, e.g., by filtration. The (2S, 3S) alcohol or (2R, 3R) alcohol as an impurity is then removed as solid. By evaporation of the solvent in the filtrate, the (2R, 3S) alcohol or (2S, 3R) alcohol can be obtained. By cooling the filtrate, the objective compound can satisfactorily be isolated by crystallization. If necessary, the solvent of the filtrate is removed by azeotropic distillation for the following reaction process. And if necessary, the filtrate is used at the following reaction process after the filtrate is concentrated or as it is.

The purification procedures described above can satisfactorily be repeated at plural times, if necessary, in case that mixtures at a high impurity content are purified. Additionally, and optionally, the purification procedures may satisfactorily be effected in combination with other purification procedures known to a person with an ordinary skill in the art. For the synthesis of the objective compound for example through reduction, as described above, the ratio of the diastereomer as an impurity can be suppressed at a certain degree by selecting an appropriate reducing agent, so that single purification procedure may afford highly purified objective compound.

According to the process (a) of the invention, the (2R, 3S) alcohol or (2S, 3R) alcohol as the objective compound can be efficiently purified and isolated by simple procedures; the content of the diastereomer as an impurity can be reduced below 6%, which is described as impossible in the above reference.

More specifically, the solid separated as insoluble matters is a solid containing the (2S, 3S) alcohol or (2R, 3R) alcohol as the principal component, although the solid generally contains a certain content of the (2R, 3S) alcohol or (2S, 3R) alcohol. The solid is purified by using known purification methods such as Soxhlet extraction, the process (a) of the invention or a combination of these methods if necessary; otherwise, these purification methods can be repeated, if necessary, to thereby afford highly purified (2S, 3S) alcohol or (2R, 3R) alcohol.

The preferable process (b) is described below.

By treating the N-carbamate-protected β-aminoalcohol represented by the general formula (1) with a base, the N-carbamate-protected β-aminoalcohol can be converted to N-carbamate-protected β-aminoepoxide as an intermediate at a progressed stage, which is represented by the general formula (2) (see the references described above).

The base preferably includes potassium hydroxide, sodium hydroxide, potassium carbonate, sodium carbonate, sodium methoxide, sodium ethoxide, potassium tert-butoxide, and sodium hydride; sodium hydroxide and potassium carbonate are particularly preferable.

The reaction solvent preferably includes protonic solvents such as methanol, ethanol, 1-propanol, 2-propanol, 1-butanol, 2-butanol, 1,2-dimethylpropanol and water or non-protonic solvents such as acetone, tetrahydrofuran and acetonitrile, singly or in mixture; ethanol, a mixture solvent of ethanol and water, a mixture solvent of 2-propanol and water, and a mixture solvent of acetone and water are particularly preferable.

The amount of the base to be used varies depending on the type of the base to be used and the combination of solvents, but the amount is generally 1 to 10 equivalents, preferably 1 to 5 equivalents. The reaction temperature varies depending on the type of the base and the combination of solvents, but the temperature is generally −10 to 80° C., preferably 0 to 60° C. The reaction time is not particularly limited, but the reaction time is preferably about 10 minutes to about 50 hours, more preferably about 30 minutes to about 40 hours, and most preferably about 1 hour to about 30 hours.

The reaction is preferably performed under agitation; after termination of the reaction, acid is satisfactorily added to quench the reaction. The acid, preferably, includes hydrochloric acid, sulfuric acid, acetic acid, citric acid and aqueous potassium hydrogen sulfate solution.

The (2R, 3S) epoxide or (2S, 3R) epoxide may be isolated from the reaction solvent by methods such as extraction, but preferably by the crystallization method at the process (d) described below. Further, so as to further remove the impurity diastereomer, the process (c) described below is preferably effected.

Preferably, for performing the process (c) or process (d) subsequent to the process (b), the reaction solvent is concentrated or substituted with an appropriate solvent, if necessary, without extraction, for use at the following process. Additionally, crystallization may be performed by the method of the process (d) after the process (b), followed by the process (c), to obtain N-carbamate-protected β-aminoepoxide crystal, again at the process (d). In such manner, the same processes can be performed at plural times, if necessary.

The preferable process (c) is described below.

N-Carbamate-protected β-aminoepoxide containing the diastereomer as an impurity, as represented by the general formula (2), is treated with an acid, to convert the impurity diastereomer to oxazolidin-2-one represented by the general formula (3), if necessary, which is then separated and removed in water or an aqueous mixture solvent.

When N-carbamate-protected β-aminoepoxide represented by the general formula (2), namely the (2R, 3S) epoxide or (2S, 3R) epoxide, is treated with an acid, the diastereomer (2S, 3S) epoxide or (2R, 3R) epoxide is relatively rapidly converted to oxazolidin-2-one derivative represented by the general formula (3) (see Reference Examples 4 and 5 described below). Because the reaction velocity of the (2R, 3S) epoxide or (2S, 3R) epoxide is slow, the diastereomer as an impurity can be removed, preferentially, by removing the resulting oxazolidin-2-one derivative from the system (Tetrahedron Letters, Vol. 35, No. 28, pp. 4939–4942, 1994).

As the acid, for example, preference is given to hydrochloric acid, hydrobromic acid, hydroiodic acid, sulfuric acid, phosphoric acid, citric acid, acetic acid, trifluoroacetic acid, methanesulfonic acid, trifluoromethanesulfonic acid, p-toluenesulfonic acid, acidic ion exchange resin (ion exchange resin acid catalyst), acid alumina (alumina acid catalyst), acid zeolite (zeolite acid catalyst) and acid china clay; solid acids insoluble in solvents such as p-toluenesulfonic acid, acid ion exchange resin, acid zeolite, and acid china clay, are preferable. Solid acids insoluble in solvents suitable for the reaction, such as acid ion exchange resin, acid alumina, acid zeolite and acid china clay are readily removed, while byproducts generated via the reaction of the epoxide with acids can be removed under filtration, simultaneously. Thus, these solid acids are particularly preferable.

The preferable reaction solvent includes methanol, ethanol, 2-propanol, 1,2-dimethylpropanol, water, acetone, tetrahydrofuran, acetonitrile, dichloromethane, chloroform, dichloroethane, diethyl ether, benzene, toluene, hexane and heptane, singly or in mixture; non-protonic solvents such as dichloromethane, toluene, acetone and acetonitrile are particularly preferable.

The quantity of acid varies, depending on the type of the acid used, and is not particularly limited. With respect to the quality (purity) and yield of the objective (2R, 3S) or (2S, 3R) epoxide, a person with an ordinary skill in the art can easily determine an appropriate amount without undue experimentation.

When p-toluenesulfonic acid is used, for example, about 1 to 5 equivalents of the acid to the (2S, 3S) or (2R, 3R) epoxide contained as an impurity is preferably used. In case that strong acid ion exchange resins and acid zeolite are used, additionally, 1 to 200% by weight of the acids is preferably used to the (2R, 3S) or (2S, 3R) epoxide to be treated.

The reaction temperature varies, depending on a combination of acids and solvents, but the reaction temperature is generally −10 to 120° C., preferably 0 to 100° C. The reaction time is preferably about 10 minutes to 50 hours, more preferably about 30 minutes to about 40 hours, and most preferably about 1 hour to about 30 hours, with no specific limitation. The objective (2R, 3S) or (2S, 3R) epoxide reacts just slowly with such acid and is converted to oxazolidin-2-one, so the reaction for a period more than necessary is not preferable. Like the quantity of the acid to be used, an appropriate reaction time can readily be determined by a person with an ordinary skill in the art, by monitoring the concentration of the diastereomer in the reaction solution, with respect to the desired quality (purity) and yield of the objective compound.

Through the acid treatment described above, the diastereomer contained as an impurity is preferentially converted to oxazolidin-2-one derivative.

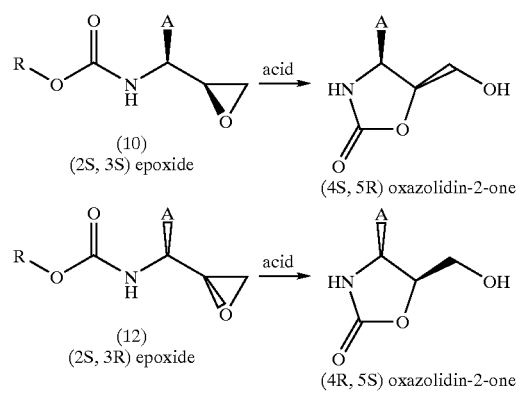

Because the oxazolidin-2-one derivative is soluble in water, the oxazolidin-2-one derivative can be readily separated and removed by dissolving the oxazolidin-2-one derivative in water or an aqueous mixture solvent. The aqueous mixture solvent means a mixture solvent of a water-miscible organic solvent with water; the organic solvent includes methanol, ethanol, 1-propanol, 2-propanol, acetone, 2-butanone, acetonitrile and tetrahydrofuran.

The method for separating and removing the oxazolidin-2-one derivative in water or an aqueous mixture solvent includes extraction or crystallization, but with no specific limitation. Wherein the process (d) is performed after the process (c), crystallization is performed in an aqueous mixture solvent, so the oxazolidin-2-one derivative is separated and removed in the mother liquor. Therefore, generally, it is not necessary to preliminarily remove the oxazolidin-2-one derivative by extraction and the like, prior to the process (d).

The preferable extraction case is described herein below. In this case, water is particularly preferable as the solvent for dissolving the oxazolidin-2-one derivative.

When solvent-soluble acids, such as p-toluenesulfonic acid, are used in the acid treatment process, for example, aqueous basic solutions such as sodium hydrogen carbonate are added under agitation, if necessary, after an appropriate reaction time, to terminate the reaction.

Thereafter, the organic layer is optionally evaporated, so as to substitute the organic layer with a solvent preferable for extraction. The extraction solvent preferably includes toluene, tert-butyl methyl ether, ethyl acetate, isopropyl acetate and dichloromethane; with respect to the separation and removal efficacy of the oxazolidin-2-one into an aqueous phase, toluene is particularly preferable. For extraction, preferably, insoluble matters in the organic layer or in the aqueous phase are preliminarily filtered off. After extraction, the organic layer is separated and preferably rinsed further in water, to efficiently remove (4S, 5R) or (4R, 5S) oxazolidin-2-one.

When solvent-insoluble acids, such as ion exchange resin and acid zeolite, are used, these acids can be removed under filtration to terminate the reaction. Thereafter, the organic solvent is optionally evaporated, so as to substitute the organic solvent with a solvent preferable for extraction. The extraction solvent preferably includes toluene, tert-butyl methyl ether, ethyl acetate, isopropyl acetate and dichloromethane; with respect to the separation and removal efficacy of the oxazolidin-2-one into the aqueous phase, toluene is particularly preferable. Then, water or aqueous mixture solvents are added for extraction; then, preferably, insoluble matters in the organic layer or in the aqueous layer are preliminarily filtered off. After extraction, the organic layer is separated and preferably rinsed further in water, to efficiently remove (4S, 5R) or (4R, 5S) oxazolidin-2-one.

By the method of the process (c) described above, the diastereomer as an impurity can be removed at a high efficiency. After the method of the process (a) of preliminarily removing the diastereomer, (2R, 3S) or (2S, 3R) epoxide, from which the diastereomer has been greatly removed, can be obtained by the process (c). Through the processes (a) and (c) of the invention or via the process (d) after these processes, the (2R, 3S) or (2S, 3R) epoxide can be obtained with a content of the diastereomer as an impurity below 3%, preferably below 2% and more preferably below 1%. The (2R, 3S) or (2S, 3R) epoxide thus afforded can be obtained as solid by evaporating the organic layer under reduced pressure. If necessary, further, the resulting solid can be purified with adsorption resins and the like. By the process (d) described below, the crystal of the (2R, 3S) or (2S, 3R) epoxide at a high purity can be recovered by such industrially advantageous method.

The preferable process (d) is described below.

Through crystallization of the (2R, 3S) or (2S, 3R) epoxide in an aqueous mixture solvent, the crystal at high purity can be obtained.

Firstly, an aqueous mixture solvent is added to the (2R, 3S) or (2S, 3R) epoxide. The aqueous mixture solvent means a mixture solvent of a water-miscible organic solvent with water; and the organic solvent includes methanol, ethanol, 1-propanol, 2-propanol, acetone, 2-butanone, acetonitrile and tetrahydrofuran. Particular preference is given to methanol, ethanol, 2-propanol, acetonitrile and acetone. The composition ratio of water and the organic solvent is not particularly limited but is preferably at 5 to 95%, more preferably at 25 to 85% (% is expressed as the ratio of the organic solvent in the mixture solvent).

The volume of the aqueous mixture solvent to be used is not particularly limited, but for example, the solvent of a volume of 2 to 20 ml to 1 g of for example the (2R, 3S) or (2S, 3R) epoxide can be used.

By subsequently cooling of the mixture, the (2R, 3S) or (2S, 3R) epoxide is crystallized.

The temperature for crystallization is preferably −40° C. to 25° C., particularly preferably −20° C. to 10° C. The crystallization then is performed, satisfactorily, under agitation or while left to stand alone. The crystallization is preferably performed under agitation, however. Generally, the (2R, 3S) or (2S, 3R) epoxide is not easily crystallized even in the aqueous mixture solvent which is comparatively good solvent for crystallizing (2R, 3S) or (2S, 3R) epoxide in comparison with other solvents. However, the crystallization may be easily performed by adding the seed crystal under the aqueous mixture solvent.

Optionally, to enhance the purification effect, the resulting crystal is heated to about 10° C. to about 40° C. to partially dissolve the crystal, which is again cooled to −20° C. to 10° C., for crystallization. The resulting crystal is preferably washed with water and the like. The process (d) enables efficient removal of the highly polar impurity into the mother liquor. Thus, highly pure (2R, 3S) or (2S, 3R) epoxide can be obtained.

Because the diastereomer (2S, 3S) or (2R, 3R) epoxide is hardly removed even by crystallization, as described above, more highly pure (2R, 3S) or (2S, 3R) epoxide can be recovered by performing the processes (a) and (b), or the process (c), or a combination of the processes (a), (b) and (c). If necessary, additionally, the process (d) may satisfactorily be carried out at plural times.

EXAMPLES

Having generally described this invention, a further understanding can be obtained by reference to certain specific examples which are provided herein for purposes of illustration only and are not intended to be limiting unless otherwise specified.

The ratios of the objective compounds and the diastereomers as described in the examples are all expressed in molar ratio.

Reference Example 1

Production of (2R, 3S)-3-tert-butoxycarbonylamino-1-chloro-2-hydroxy-4-phenylbutane Lithium aluminum tri-tert-butoxyhydride (999 mg) was added to dehydrated diethyl ether (29.3 ml); and the resulting mixture was cooled to 0° C. Subsequently, a diethyl ether solution (10 ml) of (3S)-3-tert-butoxycarbonylamino-1-chloro-4-phenyl-2-butanone (1.06 g) was dropwise added to the resulting mixture, for agitation at 0° C. for 2 hours and 20 minutes. To the reaction solution was added aqueous 5% potassium hydrogen sulfate solution, to quench the reaction, which was then subjected to extraction twice in ethyl acetate; the organic layer was washed by aqueous saturated sodium chloride solution and dried over anhydrous magnesium sulfate. After magnesium sulfate was removed, the resulting ethyl acetate solution was analyzed by HPLC. It was confirmed that the diastereomer mixture of 3-tert-butoxycarbonylamino-1-chloro-2-hydroxy-4-phenylbutane was obtained in 95% yield. The ratio of the objective (2R, 3S) compound and the diastereomer (2S, 3S) was (2R, 3S): (2S, 3S)=84.7:15.3.

The resulting solution was evaporated under reduced pressure, to afford crude (2R, 3S)-3-tert-butoxycarbonylamino-1-chloro-2-hydroxy-4-phenylbutane (1.01 g).

Example 1

Purification of (2R, 3S)-3-tert-butoxycarbonylamino-1-chloro-2-hydroxy-4-phenylbutane To the crude (2R, 3S)-3-tert-butoxycarbonylamino-1-chloro-2-hydroxy-4-phenylbutane obtained in Reference Example 1 {199.5 mg; (2R, 3S) (2S, 3R)=84.7: 15.3)}was added n-heptane (4 ml), for preparing a slurry, which was then agitated at 55° C. for one hour. The slurry solution was filtered under heating at 55° C., to remove insoluble matters. From the resulting mother liquor was evaporated the solvent under reduced pressure; the resulting residue was further dried at 40° C. under reduced pressure, to afford the crystal of (2R, 3S)-3-tert-butoxycarbonylamino-1-chloro-2-hydroxy-4-phenylbutane {the total yield of (2R, 3S) and (2S, 3R): 148.4 mg(85.2%)}. The dried crystal was analyzed by HPLC. (2R, 3S): (2S, 3S)=97.7:2.3.

$^1$H-NMR (CDCl$_3$, 300 MHz) δ ppm: 1.38 (s, 9H), 2.91 (dd, J=8.1, 13.2 Hz, 1H), 3.01 (dd, J=7.1, 13.2 Hz, 1H), 3.14 (d, J=4.0 Hz, 1H), 3.53 (s, 1H), 3.55 (d, J=2.3 Hz, 1H), 3.70–3.77 (m, 1H), 3.79–3.89 (m, 1H), 4.88 (bd, 1H), 7.19–7.35 (m, 5H)

Mass spectrum m/e: 322 (M+Na$^+$)

Example 2

Purification of (2R, 3S)-3-tert-butoxycarbonylamino-1-chloro-2-hydroxy-4-phenylbutane To the crude (2R, 3S)-3-tert-butoxycarbonylamino-1-chloro-2-hydroxy-4-phenylbutane {199.7 mg; (2R, 3S): (2S, 3S)=84.7:15.3} obtained in Reference Example 1 was added n-hexane (4 ml), for preparing a slurry, which was then agitated at 55° C. for one hour. The slurry solution was filtered under heating at 55° C., to remove insoluble matters. From the resulting mother liquor was evaporated the solvent under reduced pressure, and the resulting residue was further dried at 40° C. under reduced pressure, to afford the crystal of (2R, 3S)-3-tert-butoxycarbonylamino-1-chloro-2-hydroxy-4-phenylbutane {the total yield of (2R, 3S) and (2S, 3S): 145.0 mg (76.1%)}. The dried crystal was analyzed by HPLC. (2R, 3S): (2S, 3S)=96.0:4.0.

Example 3
Purification of (2R, 3S)-3-tert-butoxycarbonylamino-1-chloro-2-hydroxy-4-phenylbutane To the crude (2R, 3S)-3-tert-butoxycarbonylamino-1-chloro-2-hydroxy-4-phenylbutane {161.18 mg; (2R, 3S): (2S, 3S)=84.7:15.3} obtained in Reference Example 1 was added cyclohexane (3.2 ml), for preparing a slurry, which was then agitated at 50° C. for one hour and cooled to ambient temperature, followed by agitation for one hour. The slurry solution was filtered, to remove insoluble matters. From the resulting mother liquor was evaporated the solvent under reduced pressure, and the resulting residue was further dried at 40° C. under reduced pressure, to afford the crystal of (2R, 3S)-3-tert-butoxycarbonylamino-1-chloro-2-hydroxy-4-phenylbutane {the total recovery of (2R, 3S) and (2S, 3S): 112.6 mg; total yield of 77.2%} The dried crystal was analyzed by HPLC. (2R, 3S): (2S, 3S)=96.7:3.3.

Example 4
Purification of (2R, 3S)-3-tert-butoxycarbonylamino-1-chloro-2-hydroxy-4-phenylbutane To the crude (2R, 3S)-3-tert-butoxycarbonylamino-1-chloro-2-hydroxy-4-phenylbutane {200.6 mg; (2R, 3S): (2S, 3S)=84.7:15.3} obtained in Reference Example 1 was added methylcyclohexane (4 ml), for preparing a slurry, which was then agitated at 55° C. for one hour. The slurry solution was filtered under heating at 55° C., to remove insoluble matters. From the resulting mother liquor was evaporated the solvent under reduced pressure, and the resulting residue was further dried at 40° C. under reduced pressure, to afford the crystal of (2R, 3S)-3-tert-butoxycarbonylamino-1-chloro-2-hydroxy-4-phenylbutane {the total yield of (2R, 3S) and (2S, 3S): 155.0 mg(88.9%)}. The dried crystal was analyzed by HPLC. (2R, 3S): (2S, 3S)=96.3:3.7.

Reference Example 2
Production of (2S, 3R)-3-tert-butoxycarbonylamino-1-chloro-2-hydroxy-4-phenylbutane To dehydrated diethyl ether (12.6 ml) was added lithium aluminum tri-tert-butoxyhydride (457 mg), and the resulting mixture was cooled to −20° C. followed by dropwise addition of a diethyl ether solution (5.3 ml) of (3R)-3-tert-butoxycarbonylamino-1-chloro-4-phenyl-2-butanone (500 mg). The resulting mixture was stirred at −20° C. for 6 hours. To the reaction solution was added aqueous 5% potassium hydrogen sulfate solution, to quench the reaction, which was then subjected to extraction twice in ethyl acetate; the organic layer was washed by aqueous saturated sodium chloride solution and dried over anhydrous magnesium sulfate. After removal of magnesium sulfate, the resulting ethyl acetate solution was analyzed by HPLC. It was confirmed that the diastereomer mixture of 3-tert-butoxycarbonylamino-1-chloro-2-hydroxy-4-phenylbutane was obtained in 90% yield. The ratio of the objective (2S, 3R) compound and the isomer (2R, 3R) was (2S, 3R): (2R, 3R)=76.9:23.1.

The solvent was evaporated from the resulting solution under reduced pressure, to afford crude (2S, 3R)-3-tert-butoxycarbonylamino-1-chloro-2-hydroxy-4-phenylbutane (0.502 g) in solid for use as a raw material in Example 5 below.

Example 5
Purification of (2S, 3R)-3-tert-butoxycarbonylamino-1-chloro-2-hydroxy-4-phenylbutane To the crude (2S, 3R) -3-tert-butoxycarbonylamino-1-chloro-2-hydroxy-4-phenylbutane {502 mg; (2S, 3R): (2R, 3R)=76.9:23.1} obtained in Reference Example 2 was added n-hexane (10 ml) to prepare a slurry, and the resulting slurry was agitated at 55° C., for one hour. The slurry was filtered under heating at 55° C., to remove insoluble matters. From the resulting mother liquor was evaporated the solvent under reduced pressure, which was then dried at 40° C. under reduced pressure, to afford (2S, 3R)-3-tert-butoxycarbonylamino-1-chloro-2-hydroxy-4-phenylbutane in crystal {(2S, 3R) yield: 375.5 mg (94.3%)}. The resulting dried crystal was analyzed by HPLC. (2S, 3R): (2R, 3R)= 97.7:2.8.

Example 6
Production of (2R, 3S)-3-tert-butoxycarbonylamino-1,2-epoxy-4-phenylbutane (2R, 3S)-3-tert-butoxycarbonylamino-1-chloro-2-hydroxy-4-phenylbutane (100 mg) and potassium carbonate (91.5 mg) were added to methanol (2.0 ml) for agitation at ambient temperature for 4 hours. Aqueous 10% citric acid solution (0.204 ml) and water (0.408 ml) were added to the resulting mixture, from which the solvent was evaporated under reduced pressure. To the residue were added water (1 ml) and ethyl acetate (1 ml) for extraction; the organic phase was concentrated under reduced pressure, to afford (2R, 3S)-3-tert-butoxycarbonylamino-1,2-epoxy-4-{(2R, 3S) yield: 81.4 mg (93.5%)}.

$^1$H-NMR (CDCl$_3$, 300 MHz) δ ppm: 1.38 (s, 9H), 2.59 (bs, 1H), 2.69 (t, J=4.4 Hz, 1H), 2.83–3.04 (m, 3H), 4.12 (bs, 1H), 4.48 (bs, 1H), 7.17–7.37 (m, 5H)

Mass spectrum m/e: 286 (M+Na$^+$)

Example 7
Production of crystal of (2R, 3S)-3-tert-butoxycarbonylamino-1,2-epoxy-4-phenylbutane To (2R, 3S)-3-tert-butoxycarbonylamino-1-chloro-2-hydroxy-4-phenylbutane {(2R, 3S) content of 300 mg; (2S, 3S) content of 6.67 mg} obtained in the same manner as in Example 1 were added ethanol (3.40 ml), water (0.109 ml) and potassium carbonate (755 mg), for agitation at ambient temperature for 5 hours and further agitation at 30° C. for one hour. After cooling to 5° C., aqueous 17.5% citric acid solution (3.99 g) was added. After phase separation at 0° C., the ethanol layer was cooled to −10° C., followed by addition of the seed crystal and overnight agitation, to crystallize (2R, 3S)-3-tert-butoxycarbonylamino-1,2-epoxy-4-phenylbutane. The resulting slurry was filtered, to afford (2R, 3S)-3-tert-butoxycarbonylamino-1,2-epoxy-4-phenylbutane. {(2R, 3S) yield: 191 mg (71.6%) The dried crystal was analyzed by HPLC. (2R, 3S): (2S, 3S)=96.8:3.2.

Example 8
Production of crystal of (2R, 3S)-3-tert-butoxycarbonylamino-1,2-epoxy-4-phenylbutane Acetone (0.8 ml) and aqueous 2.5 mol/l sodium hydroxide solution (0.2 ml) were added to (2R, 3S)-3-tert-butoxycarbonylamino-1-chloro-2-hydroxy-4-phenylbutane {(2R, 3S) content of 97.8 mg; (2S, 3S) content of 2.2 mg} obtained in the same manner as in Example 1, for agitation at ambient temperature for 2 hours and 50 minutes. The resulting mixture was separated into phases. To the resulting acetone layer was added water (1.18 ml), which was then cooled to −10° C., followed by addition of the seed crystal and overnight agitation, to crystallize (2R, 3S)-3-tertbutoxycarbonylamino-1,2-epoxy-4-phenylbutane. The resulting slurry was filtered, to recover the crystal of (2R, 3S)-3-tert-butoxycarbonylamino-1,2-epoxy-4-phenylbutane {(2R, 3S) yield: 64.2 mg (75%)}. The dried crystal was analyzed by HPLC. (2R, 3S): (2S, 3S)=97.9:2.1.

Example 9
Production of (2R, 3S)-3-tert-butoxycarbonylamino-1,2-epoxy-4-phenylbutane 2-Propanol (342 ml) and aqueous 2.5 mol/l sodium hydroxide solution (85.8 ml) were added to (2R, 3S)-3-tert-butoxycarbonylamino-1-chloro-2-hydroxy-4-phenylbutane {(2R, 3S) content of 40.6 g; (2S, 3S) content of 1.66 g} obtained in the same manner as in Example 1, for agitation at 0° C. for 1.5 hours. Aqueous 13.8% citric acid solution (99.5 g) was added to the resulting mixture, and then, 2-propanol was evaporated under reduced pressure. To the resulting residue was added toluene (342 ml) for extraction; and the organic layer was concentrated under reduced pressure, to afford (2R, 3S)-3-tert-butoxycarbonylamino-1,2-epoxy-4-phenylbutane (37.2 g) {the total yield of (2R, 3S) and (2S, 3S): 98.3%}, which was then analyzed by HPLC. (2R, 3S): (2S, 3R)=96.1:3.9.

Example 10
Purification of (2R, 3S)-3-tert-butoxycarbonylamino-1,2-epoxy-4-phenylbutane Toluene (5.4 ml) and p-toluene sulfonic acid monohydrate (25.9 mg) were added to (2R, 3S)-3-tert-butoxycarbonylamino-1,2-epoxy-4-phenylbutane (2R, 3S) content of 443.3 mg; (2S, 3S) content of 11.9 mg} obtained in the same manner as in Example 9, for agitation at 18° C. for 2 hours. Aqueous saturated sodium hydrogen carbonate solution was added to the reaction mixture to quench the reaction, and then, the organic layer was washed by aqueous saturated sodium chloride solution, dried over anhydrous magnesium sulfate and filtered. The filtrate was analyzed by HPLC. (2R, 3S): (2S, 3S)=99.6:0.4; additionally, the recovery yield of (2R, 3S)-3-tert-butoxycarbonylamino-1,2-epoxy-4-phenylbutane was 77.5%.

A part of the filtrate {containing 229.4 mg of (2R, 3S)-3-tert-butoxycarbonylamino-1,2-epoxy-4-phenylbutane} was charged and concentrated, which was then separated and purified on a column packed with a synthetic adsorption resin CHP20P (29 ml; Mitsubishi Chemical). The resulting fraction was concentrated and extracted in n-heptane. The organic layer was concentrated, to afford (2R, 3S)-3-tertbutoxycarbonylamino-1,2-epoxy-4-phenylbutane in solid {(2R, 3S) yield: 198 mg (86.5%)}. The solid was analyzed by HPLC. (2R, 3S):(2S, 3S)=99.6:0.4.

Example 11
Acid Treatment of (2R, 3S)-3-tert-butoxycarbonylamino-1,2-epoxy-4-phenylbutane To (2R, 3S)-3-tert-butoxycarbonylamino-1,2-epoxy-4-phenylbutane obtained in Example 9 {(2R, 3S) content of 35.7 g; (2S, 3S) content of 1.45 g} were added dichloromethane (416 ml) and Amberlyst® (Aldrich; 15 ion exchange resin; 25.0 g); the mixture was agitated at ambient temperature for 2 hours and 50 minutes. Amberlist was removed by filtration; the filtrate was concentrated under reduced pressure, to remove the solvent. Toluene (200 ml) and water (200 ml) were added to the resulting residue, to remove insoluble matters under filtration. The filtrate was subjected to phase separation, which was dried by using anhydrous sodium sulfate. From the resulting layer was evaporated the solvent under reduced pressure. Furthermore, n-heptane (20 ml) was added to the residue, from which the solvent was removed under reduced pressure, to afford (2R, 3S)-3-tert-butoxycarbonylamino-1,2-epoxy-4-phenylbutane {(2R, 3S) yield: 23.4 g (66%)}. HPLC analysis showed that (2R, 3S): (2S, 3S)=99.2:0.8.

Example 12
Acid Treatment of (2R, 3S)-3-tert-butoxycarbonylamino-1,2-epoxy-4-phenylbutane To (2R, 3S)-3-tert-butoxycarbonylamino-1,2-epoxy-4-phenylbutane obtained in the same manner as in Example 9 { (2R, 3S) content of 92.8 mg; (2S, 3S) content of 2.2 mg} were added toluene (2 ml) and Amberlyst® (Aldrich; 15 ion exchange resin; 28.9 mg); the mixture was agitated at 40° C. for 29 hours, followed by addition of Amberlist (29.5 mg) and agitation at 60° C. for 19 hours. The reaction solution was analyzed by HPLC. (2R, 3S):(2S, 3S)=99.5:0.5. The recovery yield of (2R, 3S)-3-tert-butoxycarbonylamino-1,2-epoxy-4-phenylbutane was 81.3%.

Example 13
Purification of (2R, 3S)-3-tert-butoxycarbonylamino-1,2-epoxy-4-phenylbutane Dichloromethane (0.6 ml) and zeolite (Zeolyst International; Zeolyst® CBV90A; 71 mg) were added to (2R, 3S)-3-tert-butoxycarbonylamino-1,2-epoxy-4-phenylbutane {(2R, 3S) content of 20.7 mg; (2S, 3S) content of 0.7 mg} obtained in the same manner as in Example 9, for agitation at ambient temperature for 6.5 hours. The reaction solution was analyzed by HPLC. (2R, 3S): (2S, 3S)=99.6:0.4; additionally, the recovery yield of (2R, 3S)-3-tert-butoxycarbonylamino-1,2-epoxy-4-phenylbutane was 80.9%.

Example 14
Production of (2R, 3S)-3-tert-butoxycarbonylamino-1,2-epoxy-4-phenylbutane crystal Methanol (30.5 ml) and water (20.5 ml) were added to (2R, 3S)-3-tert-butoxycarbonylamino-1,2-epoxy-4-phenylbutane {(2R, 3S) content of 11.1 g; (2S, 3S) content of 75.5 mg; (2R, 3S) purity=95.3%; HPLC area ratio} obtained by the same method as in Example 11. The resulting mixture was cooled to −10° C., followed by addition of the seed crystal for overnight agitation, to crystallize (2R, 3S)-3-tert-butoxycarbonylamino-1,2-epoxy-4-phenylbutane. After addition of methanol (17.3 ml) at −10° C., the temperature was raised to 0° C. for agitation for one hour, followed by cooling again to −10° C. The resulting slurry was filtered and washed by 70% methanol (5 ml) at −10° C., to afford (2R, 3S)-3-tert-butoxycarbonylamino-1,2-epoxy-4phenylbutane in crystal (6.78 g) {the total yield of (2R, 3S) and (2S, 3S) was 61.1%}. The HPLC analysis shows (2R, 3S): (2S, 3S)=99.5:0.5. Additionally, the purity was 98.0% (HPLC area ratio).

Example 15
Production of (2R, 3S)-3-tert-butoxycarbonylamino-1,2-epoxy-4-phenylbutane crystal Methanol (7.7 ml) and water (5.1 ml) were added to (2R, 3S)-3-tert-butoxycarbonylamino-1,2-epoxy-4-phenylbutane {(2R, 3S) content of 2.94 g; (2S, 3S) content of 14.8 mg; (2R, 3S) purity=98.0%; HPLC area ratio} obtained in Example 14. The resulting mixture was cooled to −10° C., followed by addition of the seed crystal for agitation, to crystallize (2R, 3S)-3-tert-butoxycarbonylamino-1,2-epoxy-4-phenylbutane. The temperature was raised to ambient temperature, followed by addition of methanol (6.4 ml) and water (0.9 ml) and further agitation for 15 minutes; and the resulting mixture was again cooled to −10° C. The resulting slurry was filtered and washed by 70% methanol (6 ml) at −10° C., to afford (2R, 3S)-3-tert-butoxycarbonylamino-1, 2-epoxy-4-phenylbutane in crystal (2.03 g) {the total yield of (2R, 3S) and (2S, 3S) was 67.2%}. The HPLC analysis shows (2R, 3S): (2S, 3S)=99.6:0.4. Additionally, the purity was 99.3% by HPLC (HPLC area ratio).

$^1$H-NMR (CDCl$_3$,300 MHz) δ ppm: 1.38 (s, 9H), 2.59 (bs, 1H), 2.69 (t, J=4.4 Hz, 1H), 2.83–3.04 (m, 3H), 4.12 (bs, 1H), 4.48 (bs, 1H), 7.17–7.37 (m, 5H)

Mass spectrum m/e: 286 (M+Na$^+$)
{α}$_D$$^{20}$=−15.2° (c=1.0, MeOH)
Melting point: 46 to 47° C.

Reference Example 3
Production of (2R, 3S)-3-tert-butoxycarbonylamino-1-chloro-2-hydroxy-4-phenylbutane Lithium aluminum tri-tert-butoxyhydride (28.2 g) was added to dehydrated diethyl ether (600 ml) in argon atmosphere, and the resulting mixture was cooled to 0° C., followed by addition of (3S)-3-tert-butoxycarbonylamino-1-chloro-4-phenyl-2-butanone (30.0 g), for agitation at 0° C. for 2.5 hours. To the reaction solution was added aqueous 1N hydrochloric acid solution (222 ml), to quench the reaction; the organic layer was washed by aqueous 1N hydrochloric acid solution and aqueous saturated sodium chloride solution; and the resulting organic layer was analyzed by HPLC. It was confirmed that the diastereomer mixture of 3-tert-butoxycarbonylamino-1-chloro-2-hydroxy-4-phenylbutane was obtained in 92.0% yield. The ratio of the objective (2R, 3S) and the diastereomer (2S, 3S) generated was (2R, 3S): (2S, 3S)=87.4:12.6.

From the resulting solution was evaporated the solvent under reduced pressure, to afford crude (2R, 3S)-3-tertbutoxycarbonylamino-1-chloro-2-hydroxy-4-phenylbutane (33.2 g).

Example 16
Purification of (2R, 3S)-3-tert-butoxycarbonylamino-1-chloro-2-hydroxy-4-phenylbutane and production of (2R, 3S)-3-tert-butoxycarbonylamino-1,2-epoxy-4-phenylbutane 2-Propanol (62.1 ml) and water (20.7 ml) were added to (2R, 3S)-3-tert-butoxycarbonylamino-1-chloro-2hydroxy-4-phenylbutane (33.2 g) {(2R, 3S):(2S, 3S)=87.4:12.6} obtained in Reference Example 3, for agitation at 70° C. for one hour. The resulting solution was cooled over 10 hours to 20° C. Insoluble matters generated under cooling was removed under filtration at 20° C. 2-Propanol (143 ml) and aqueous 3.26 mol/l sodium hydroxide solution (42.3 ml) were added to the resulting mother liquor, followed by agitation at 4° C. f or 2 hours. The reaction solution was analyzed by HPLC. The objective (2R, 3S) compound was at 93.9% (HPLC area ratio). After the reaction was quenched by the addition of aqueous 1.06% citric acid solution, water (73.2 ml) was added. After cooling from 27° C. to −10° C. over 2.5 hours, the addition of the seed crystal and overnight agitation enabled the crystallization of (2R, 3S)-3-tert-butoxycarbonylamino-1,2-epoxy-4-phenylbutane. By filtration of the resulting slurry, the crystal (20.4 g) of (2R, 3S)-3-tert-butoxycarbonylamino-1,2-epoxy-4-phenylbutane was obtained {the yield of(2R, 3S): 85.0%}. The dried crystal was then analyzed by HPLC. (2R, 3S): (2S, 3S)=97.9:2.1. Additionally, the purity of (2R, 3S) was 96.4% (HPLC area ratio).

Example 17
Purification of (2R, 3S)-3-tert-butoxycarbonylamino-1-chloro-2-hydroxy-4-phenylbutane 2-Propanol (8.1 ml) and water (2.7 ml) were added to (2R, 3S)-3-tert-butoxycarbonylamino-1-chloro-2-hydroxy-4-phenylbutane {(2R, 3S) content of 3.05 g; (2S, 3S) content of 0.55 g; (2R, 3S): (2S, 3S)=84.7:15.3} obtained in the same manner as in Reference Example 3, to prepare a slurry, for agitation at 60° C. for one hour, which was then cooled to 24° C. over 1.3 hours. The slurry was filtered at 24° C., to remove insoluble matters. The resulting mother liquor was analyzed by HPLC. (2R, 3S)-3-tert-butoxycarbonylamino-1-chloro-2-hydroxy-4-phenylbutane (2.8 g) was obtained in 91.3% recovery yield. (2R, 3S):(2S, 3S)=97.1:2.9. Additionally, the purity of (2R, 3S) was at 94.4% (HPLC area ratio).

Example 18
Production of (2R, 3S)-3-tert-butoxycarbonylamino-1,2-epoxy-4-phenylbutane 2-Propanol (12.9 ml) and aqueous 6.08 mol/l sodium hydroxide solution (2.94 g) were added to a solution containing (2R, 3S)-3-tert-butoxycarbonylamino-1-chloro-2-hydroxy-4-phenylbutane obtained in Example 17 {(2R, 3S) content of 2.79 g; (2S, 3S) content of 83.9 mg}, for agitation at 4° C. for 15 hours. The resulting solution was analyzed by HPLC, which indicates that the objective (2R, 3S) compound was at 94.0% (HPLC area ratio). After the reaction was quenched by the addition of aqueous 4.4% citric acid solution (20.9 g), the reaction solution was cooled from 25° C. to −10° C. over 2.3 hours; then, the seed crystal was added, followed by addition of water (19.2 ml) for overnight agitation, to crystallize (2R, 3S)-3-tert-butoxycarbonylamino-1,2-epoxy-4-phenylbutane. By filtration of the resulting slurry, the crystal of the objective (2R, 3S)-3-tert-butoxycarbonylamino-1,2-epoxy-4-phenylbutane was obtained {(2R, 3S) yield: 2.4 g (96.2%)}. The dried crystal was then analyzed by HPLC. (2R, 3S): (2S, 3S)=97.9:2.1. Additionally, the purity of (2R, 3S) was at 95.4% (HPLC area ratio).

Example 19
Purification of (2R, 3S)-3-tert-butoxycarbonylamino-1-chloro-2-hydroxy-4-phenylbutane Acetone (4.68 ml) and water (1.56 ml) were added to (2R, 3S)-3-tert-butoxycarbonylamino-1-chloro-2-hydroxy-4-phenylbutane {(2R, 3S) content of 1.33 g; (2S, 3S) content of 0.34 g} obtained by the same method as in Reference Example 3, to prepare a slurry, which was then agitated at ambient temperature for 2.5 hours. The slurry was filtered at ambient temperature, to remove insoluble matters. The resulting mother liquor was analyzed by HPLC. The recovery yield of (2R, 3S)-3-tert-butoxycarbonylamino-1-chloro-2-hydroxy-4-phenylbutane was 74.5% (0.99 g) (2R, 3S): (2S, 3S)=96.6:3.4.

Example 20
Purification of (2R, 3S)-3-tert-butoxycarbonylamino-1-chloro-2-hydroxy-4-phenylbutane and production of (2R, 3S)-3-tert-butoxycarbonylamino-1,2-epoxy-4-phenylbutane 2-Propanol (25.3 ml) and water (8.5 ml) were added to (2R, 3S)-3-tert-butoxycarbonylamino-1-chloro-2-hydroxy-4-phenylbutane {(2R, 3S) content of 11.28 g; (2S, 3S) content of 1.55 g} obtained by the same method as in Reference Example 3, to prepare a slurry, followed by addition of potassium chloride (329 mg) at 70° C., which was then agitated for 15 hours and cooled to 20° C. over 2.5 hours. The slurry was filtered at 20° C., to remove insoluble matters. 2-Propanol (58.7 ml) and water (3.2 ml) were added to the resulting mother liquor, followed by cooling at 4° C. and addition of aqueous 4 mol/l sodium hydroxide solution (14.1 ml), for agitation at 4° C. for 2.5 hours. The reaction solution was analyzed by HPLC. The objective (2R, 3S) compound was at 93.6% (HPLC area ratio). The reaction was quenched by addition of aqueous 0.85% citric acid solution (142 g). After cooling from 27° C. to −10° C. for 2.5 hours, the addition of the seed crystal and overnight agitation enabled the crystallization of (2R, 3S)-3-tertbutoxycarbonylamino-1,2-epoxy-4-phenylbutane. The resulting slurry was filtered; to the resulting crystal was added water (56.4 ml), to prepare a slurry, followed by agitation at 20° C. for one hour; the slurry was filtered and dried, to afford the crystal of (2R, 3S)-3-tert-butoxycarbonylamino-1,2-epoxy-4-phenylbutane {(2R, 3S) recovery yield of 7.94g (80.2%)}. The dried crystal was analyzed by HPLC. (2R, 3S):(2S, 3S)=98.1:1.9. Additionally, (2R, 3S) purity was at 97.6% (HPLC area ratio).

Example 21
Purification of (2R, 3S)-3-tert-butoxycarbonylamino-1,2-epoxy-4-phenylbutane Acetonitrile (48.5 ml) and zeolite (Zeolyst International; Zeolyst® CBV600; 4.05 g) were added to (2R, 3S)-3-tert-butoxycarbonylamino-1,2-epoxy-4-phenylbutane {(2R, 3S) content of 7.94 g; (2S, 3S) content of 154 mg} obtained in Example 20, for agitation at ambient temperature for 24 hours. The reaction solution was analyzed by HPLC. The objective (2R, 3S) compound was at 87.0% (HPLC area ratio). The reaction solution was filtered through celite; to the resulting mother liquor was added water (161 ml), and the mixture was then cooled from 25° C. to −5° C. over 5 hours. The addition of the seed crystal and overnight agitation enabled the crystallization of (2R, 3S)-3-tert-butoxycarbonylamino-1,2-epoxy-4-phenylbutane. The slurry was filtered and dried, to afford the crystal of (2R, 3S)-3-tert-butoxycarbonylamino-1,2-epoxy-4-phenylbutane { (2R, 3S) yield: 5.56 g (68.7%)}. The dried crystal was analyzed by HPLC. (2R, 3S): (2S, 3S)=99.5:0.5; additionally, the purity of (2R, 3S) was at 97.5% (HPLC area ratio).

Reference Example 4
Production of (4S, 5R)-5-hydroxymethyl-4-phenylmethyloxazolidin-2-one Ethanol (27.5 ml) was added to (2S, 3S)-3-tert-butoxycarbonylamino-1,2-epoxy-4-phenylbutane (2.75 g), followed by addition of aqueous 6.8% citric acid solution (29.5 g) and agitation at 70° C. for 2 hours. After cooling to ambient temperature, ethanol was removed under reduced pressure. The product was extracted by using ethyl acetate, followed by drying over anhydrous sodium sulfate and concentration under reduced pressure. Furthermore, a mixture solvent of hexane (2.5 ml) and ethyl acetate (2.5 ml) was added, to generate crystal. The crystal was filtered, and then, the crystal was rinsed twice by using a mixture solvent of hexane/ethyl acetate (1/1). The resulting crystal was dried, to afford the objective (4S, 5R)-5-hydroxymethyl-4-phenylmethyloxazolidin-2-one (1.79 g) in 80% yield.

$^1$H-NMR (DMSO-d6, 300 MHZ) δ ppm: 2.73–2.86 (m, 2H), 3.20 (dt, 1H, J=12.3, 5.1 Hz), 3.30–3.41 (m, 1H), 3.80 (ddd, 1H, J=5.7, 5.7, 5.7 Hz), 4.13–4.18 (ddd, 1H, J=5.7, 5.7, 5.7 Hz), 5.01 (dd, 1H, J=5.7, 5.7 Hz), 7.17–7.37 (m, 5H)

$^{13}$C-NMR (DMSO-d6, 300 MHz) δ ppm: 40.4, 54.1, 61.9, 80.5, 126.7, 128.5, 129.7, 136.6, 158.1

Mass spectrum m/e: 208 (M+Na$^+$)
{α}D$^{20}$=−47.20° (c=1.0. MeOH)

Reference Example 5

Production of (4S, 5R)-5-hydroxymethyl-4-phenylmethyloxazolidin-2-one

Example 22
Purification of (2R, 3S)-3-tert-butoxycarbonylamino-1-chloro-2-hydroxy-4-phenylbutane Toluene (5.0 ml) was added to (2R, 3S)-3-tert-butoxycarbonylamino-1-chloro-2-hydroxy-4-phenylbutane {(2R, 3S) content of 0.818 g; (2S, 3S) content of 0.162 g} { (2R, 3S):(2S, 3S)=83.4:16.6} obtained by the same method as in Reference Example 3, to prepare a slurry, which was then agitated at 70° C. for 0.5 hour and cooled to 10° C. over 10 hours. The slurry was filtered at 10° C., to remove insoluble matters. The resulting mother liquor was analyzed by HPLC. (2R, 3S)-3-tert-Butoxycarbonylamino-1-chloro-2-hydroxy-4-phenylbutane (0.745 g) was obtained in 91.1% recovery yield. (2R, 3S):(2S, 3S)=98.8:1.2.

Example 23
Purification of (2R, 3S)-3-tert-butoxycarbonylamino-1-chloro-2-hydroxy-4-phenylbutane Chlorobenzene (14.0 ml) was added to (2R, 3S)-3-tert-butoxycarbonylamino-1-chloro-2-hydroxy-4-phenylbutane {(2R, 3S) content of 1.59 g; (2S, 3S) content of 0.22 g} {(2R, 3S):(2S, 3S)=88.0:12.0} obtained by the same method as in Reference Example 3, to prepare a slurry, which was then agitated at 70° C. for 0.5 hour and cooled to 10° C. over 10 hours. The slurry was filtered at 10° C., to remove insoluble matters. The resulting mother liquor was analyzed by HPLC. (2R, 3S)-3-tert-Butoxycarbonylamino-1-chloro-2-hydroxy-4-phenylbutane (1.15g) was obtained in 94.9% recovery yield. (2R, 3S): (2S, 3S)=98.4:1.6.

Example 24
Purification of (2R, 3S)-3-tert-butoxycarbonylamino-1-chloro-2-hydroxy-4-phenylbutane Xylene (the mixture of 10% o-xylene, 70% m-xylene, 10% p-xylene, 10% ethylbenzene) (14.0 ml) was added to (2R, 3S)-3-tert-butoxycarbonylamino-1-chloro-2-hydroxy-4-phenylbutane {(2R, 3S) content of 1.59 g; (2S, 3S) content of 0.22 g} {(2R, 3S): (2S, 3S)=88.0:12.0} obtained by the same method as in Reference Example 3, to prepare a slurry, which was then agitated at 70° C. for 0.5 hour and cooled to 10° C. over 10 hours. The slurry was filtered at 10° C., to remove insoluble matters. The resulting mother liquor was analyzed by HPLC. (2R, 3S)-3-tert-Butoxycarbonylamino-1-chloro-2-hydroxy-4-phenylbutane (1.33 g) was obtained in 83.5% recovery yield. (2R, 3S): (2S, 3S)=98.7:1.3.

Example 25
Purification of (2R, 3S)-3-tert-butoxycarbonylamino-1-chloro-2-hydroxy-4-phenylbutane Benzene (14.0 ml) was added to (2R, 3S)-3-tert-butoxycarbonylamino-1-chloro-2-hydroxy-4-phenylbutane {(2R, 3S) content of 1.59 g; (2S, 3S) content of 0.22 g} { (2R, 3S) (2S, 3S)=88.0:12.0} obtained by the same method as in Reference Example 3, to prepare a slurry, which was then agitated at 70° C. for 0.5 hour and cooled to 10° C. over 10 hours. The slurry was filtered at 10° C., to remove insoluble matters. The resulting mother liquor was analyzed by HPLC. (2R, 3S)-3-tert-Butoxycarbonylamino-1-chloro-2-hydroxy-4-phenylbutane (1.43 g) was obtained in 89.9% recovery yield. (2R, 3S):(2S, 3S)=97.0:3.0.

Example 26

Production of crystal of (2R, 3S)-3-tert-butoxycarbonylamino-1,2-epoxy-4-phenylbutane The solution of (2R, 3S)-3-tert-butoxycarbonylamino-1-chloro-2-hydroxy-4-phenylbutane {(2R, 3S) content of 5.99 g; (2S,3S) content of 80 mg} obtained in the same manner as in Example 22 was concentrated, and then 2-propanol (30.8 ml) and water (10.3 ml) were added to the resulting residue. After cooling to 4° C., 4 mol/l sodium hydroxide solution (7.7 ml) was added, followed by agitation at 4° C. for 70 minutes. The reaction solution was analyzed by HPLC. The objective (2R, 3S) compound was at 97.1% (HPLC area ratio). After the reaction was quenched by the addition of aqueous 1.5% citric acid solution, the resulting mixture was cooled to −3° C., followed by the addition of the seed crystal and agitation for 30 minutes. The mixture was cooled to −10° C. over 1 hour and was agitated for 2 hours, to crystallize (2R, 3S)-3-tert-butoxycarbonylamino-1,2-epoxy-4-phenylbutane. After filtration of the resulting slurry, water (61.6 ml) was added to the resulting crystal, for preparing slurry, which was then agitated at ambient temperature for 30 minutes, to filtrate the slurry. The resulting crystal was dried to obtain the objective crystal of (2R, 3S)-3-tert-butoxycarbonylamino-1,2-epoxy-4-phenylbutane {the yield of (2R,3S): 4.92 g (93.5%)}. The dry crystal was analyzed by HPLC. (2R, 3S): (2S, 3S)=97.9:2.1. Additionally, the purity of (2R, 3S) was 98.3% (HPLC area ratio).

Example 27

Purification of (2R, 3S)-3-tert-butoxycarbonylamino-1,2-epoxy-4-phenylbutane

Acetonitrile (15 ml) and zeolite (Zeolyst International; Zeolyst® CBV400; 2.50 g) were added to (2R, 3S)-3-tert-butoxycarbonylamino-1,2-epoxy-4-phenylbutane {(2R, 3S) content of 2.46 g; (2S, 3S) content of 37.5 mg} obtained in Example 26, for agitation at 25° C. for 5.5 hours. The reaction solution was analyzed by HPLC. The objective (2R, 3S) compound was at 78.7% (HPLC area ratio). The reaction solution was filtrated through celite and then the celite was washed by acetonitrile. The resulting mother liquor was concentrated to obtain oil. Acetonitrile (11.5 ml) and water (38.5 ml) were added to the oil, and the mixture was cooled from ambient temperature to −5° C. over 4 hours. The seed crystal was added to the mixture and the mixture was agitated for 3 hours, to crystallize (2R, 3S)-3-tert-butoxycarbonylamino-1,2-epoxy-4-phenylbutane. The slurry was filtered; to the resulting crystal was added water (25 ml), to prepare a slurry again, followed by agitation at ambient temperature for 30 minutes; the slurry was filtered and dried, to afford the crystal of (2R, 3S)-3-tert-butoxycarbonylamino-1,2-epoxy-4-phenylbutane {(2R, 3S)yield: 1.56 g (63.2%)}. The dried crystal was analyzed by HPLC. (2R, 3S):(2S, 3S)=99.7:0.3; additionally, the purity of (2R, 3S) was at 98.8% (HPLC area ratio).

Advantages of the Invention

As has been described above, embodiments of the invention may facilitate production of highly pure (2R, 3S)- or (2S, 3R)-N-carbamate-protected β-aminoepoxide or (2R, 3S) or (2S, 3R)-N-carbamate-protected β-aminoalcohol by an efficient and industrially advantageous method of the invention.

The entire contents of each of the aforementioned references, patents, applications and published applications are hereby incorporated by reference, the same as if set forth at length.

This application is based on Japanese Patent Application Nos. 245645/1999, filed on Aug. 31, 1999, 035074/2000, filed on Feb. 14, 2000, 082895/2000, filed on Mar. 23, 2000, and 199234/2000, filed on Jun. 30, 2000, the entire contents of each of which are hereby incorporated by reference, the same as if set forth at length.

Obviously, numerous modifications and variations of the present invention are possible in light of the above teachings. It is therefore to be understood that within the scope of the appended claims, the invention may be practiced otherwise than as specifically described herein.

What is claimed is:

1. A method for producing an N-carbamate-protected β-aminoepoxide crystal, comprising:

(a) dissolving N-carbamate-protected β-aminoalcohol comprising at least a diastereomer thereof as an impurity and being represented by the formula (1), in at least one solvent selected from the group consisting of aromatic hydrocarbon, aryl halide, cyclohexane, aqueous mixture, acetone and 2-propanol, to remove insoluble material:

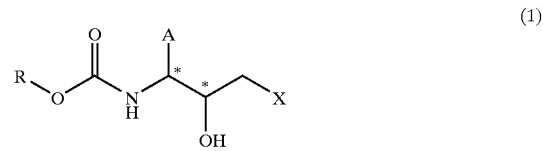

wherein in formula (1):

R represents a lower alkyl group, benzyl group or fluorenylmethyl group;

A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone;

X represents halogen atom;

* represents asymmetric carbon atom; and wherein the steric configuration at 2- and 3-positions is (2R, 3S) or (2S, 3R); and said diastereomer which exists as an impurity has a steric configuration of (2R, 3R) or (2S, 3S);

(b) treating the N-carbamate-protected β-aminoalcohol represented by the formula (1) with a base, thereby converting the N-carbamate-protected β-aminoalcohol to N-carbamate-protected β-aminoepoxide represented by the formula (2):

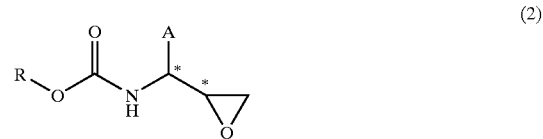

wherein in formula (2), R, A and * have the same meanings as recited above; and wherein the steric configuration at 2- and 3-positions is (2R, 3S) or (2S, 3R) and wherein said N-carbamate-protected β-aminoepoxide represented by formula (2) comprises as an impurity a diastereomer having the configuration of (2R, 3R) or (2S, 3S);

(c) treating the N-carbamate-protected β-aminoepoxide comprising at least a diastereomer thereof as an impurity and being represented by the formula (2) with an acid, thereby converting the diastereomer which has the configuration of(2R, 3R) or (2S, 3S) to an oxazolidin-2-one derivative represented by the formula (3):

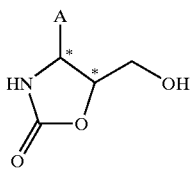

(3)

wherein in formula (3), A and * have the same meaning as recited above; and wherein the steric configuration at 4- and 5-positions is (4S, 5R) or (4R, 5S), and optionally separating and removing the resulting oxazolidin-2-one derivative in water or an aqueous mixture solvent; and (d) crystallizing the N-carbamate-protected aminoepoxide represented by the formula (2) in an aqueous mixture solvent, to obtain crystals of said N-carbamate-protected aminoepoxide having the configuration (2R, 3S) or (2S, 3R).

2. The method according to claim 1, wherein A is benzyl group.

3. The method according to claim 1, wherein R is tert-butyl group.

4. The method according to claim 1, wherein in step (a), the aromatic hydrocarbon solvent is at least one selected from the group consisting of toluene, chlorobenzene, xylene and benzene; the aqueous mixture solvent is a mixture solvent of at least one organic solvent selected from the group consisting of methanol, ethanol, 1-propanol, 2-propanol, acetone, 2-butanone, acetonitrile and tetrahydrofuran, and water.

5. The method according to claim 1, wherein in step (a), the aromatic hydrocarbon solvent is at least one selected from the group consisting of toluene and xylene; and the aqueous mixture solvent is a mixture solvent of at least one organic solvent selected from the group consisting of methanol, ethanol and 2-propanol, and water.

6. The method according to claim 1, wherein the solvent in step (a) is selected from the group consisting of toluene, xylene and a mixture solvent of 2-propanol and water.

7. The method according to claim 1, wherein in step (c), the acid is a solid acid insoluble in solvents.

8. The method according to claim 1, wherein in step (d), the aqueous mixture solvent is a mixture solvent of at least one organic solvent selected from the group consisting of acetone, methanol, ethanol, 2-propanol and acetonitrile, and water.

9. A method for producing an N-carbamate-protected β-aminoalcohol, comprising:

(a) dissolving N-carbamate-protected β-aminoalcohol comprising at least a diastereomer thereof as an impurity and represented by the formula (1) in at least one solvent selected from the group consisting of aromatic hydrocarbon, cyclohexane, aqueous mixture, acetone and 2-propanol, to remove insoluble materials:

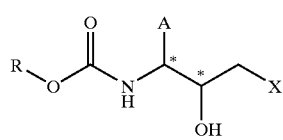

(1)

wherein in formula (1):
R represents a lower alkyl group, benzyl group or fluorenylmethyl group;

A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone;
X represents halogen atom; and
* represents asymmetric carbon atom;
wherein the steric configuration at 2- and 3-positions is (2R, 3S) or (2S, 3R).

10. The method according to claim 9, wherein A is benzyl group.

11. The method according to claim 9, wherein R is tert-butyl group.

12. The method according to claim 9, wherein in step (a), the aromatic hydrocarbon solvent is at least one selected from the group consisting of toluene, chlorobenzene, xylene and benzene; and the aqueous mixture solvent is a mixture solvent of at least one organic solvent selected from the group consisting of methanol, ethanol, 1-propanol, 2-propanol, acetone, 2-butanone, acetonitrile and tetrahydrofuran, and water.

13. The method according to claim 9, wherein in step (a), the aromatic hydrocarbon solvent is at least one selected from the group consisting of toluene and xylene; and the aqueous mixture solvent is a mixture solvent of at least one organic solvent selected from the group consisting of methanol, ethanol and 2-propanol, and water.

14. The method according to claim 9, wherein the solvent in step (a) is at least one selected from the group consisting of toluene, xylene, and a mixture solvent of 2-propanol and water.

15. A method for producing an N-carbamate-protected β-aminoepoxide, comprising:

(a) dissolving N-carbamate-protected β-aminoalcohol comprising at least a diastereomer thereof as an impurity and represented by the formula (1), in at least one solvent selected from the group consisting of aromatic hydrocarbon, cyclohexane, aqueous mixture solvent, acetone and 2-propanol, to remove insoluble materials:

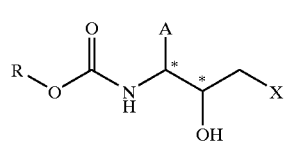

(1)

wherein in formula (1):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone;
X represents halogen atom; and
* represents asymmetric carbon atom;
wherein the steric configuration at 2- and 3-positions is (2R, 3S) or (2S, 3R);

(b) treating the N-carbamate-protected β-aminoalcohol represented by the formula (1) with a base, thereby converting the N-carbamate-protected β-aminoalcohol to N-carbamate-protected β-aminoepoxide represented by the formula (2):

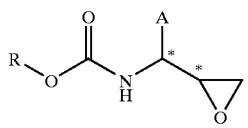
(2)

wherein in formula (2), R, A and * have the same meanings as recited above; and wherein the steric configuration at 2- and 3-positions is (2R, 3S) or (2S, 3R).

16. The method according to claim 15, wherein A is benzyl group.

17. The method according to claim 15, wherein R is tert-butyl group.

18. The method according to claim 15, wherein in step (a), the aromatic hydrocarbon solvent is at least one selected from the group consisting of toluene, chlorobenzene, xylene and benzene; and wherein the aqueous mixture solvent is a mixture solvent of at least one organic solvent selected from the group consisting of methanol, ethanol, 1-propanol, 2-propanol, acetone, 2-butanone, acetonitrile and tetrahydrofuran, and water.

19. The method according to claim 15, wherein in step (a) the aromatic hydrocarbon solvent is at least one selected from the group consisting of toluene and xylene; and wherein the aqueous mixture solvent is a mixture solvent of at least one organic solvent selected from the group consisting of methanol, ethanol and 2-propanol, and water.

20. The method according to claim 15, wherein the solvent in step (a) is selected from the group consisting of toluene, xylene, and a mixture solvent of 2-propanol and water.

21. A method for producing an N-carbamate-protected β-aminoepoxide crystal, comprising:
(c) treating the N-carbamate-protected β-aminoepoxide comprising at least a diastereomer thereof as an impurity and represented by the formula (2):

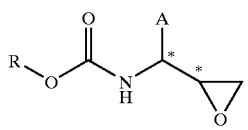
(2)

wherein in formula (2):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone;
* represents asymmetric carbon atom; and wherein the steric configuration at 2- and 3-positions is (2R, 3S) or (2S, 3R); and
said diastereomer which exists as an impurity has a steric configuration of (2R, 3R) or (2S, 3S); with an acid, thereby converting the diastereomer which has the configuration of (2R, 3R) or (2S, 3S) to an oxazolidin-2-one derivative represented by the formula (3):

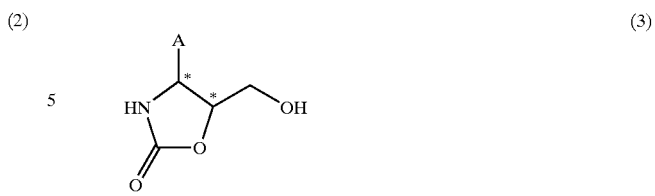
(3)

wherein in formula (3), A and * have the same meaning as recited above; and wherein the steric configuration at 4- and 5-positions is (4S, 5R) or (4R, 5S), and optionally separating and removing the resulting oxazolidin-2-one derivative in water or an aqueous mixture solvent; and
(d) crystallizing the N-carbamate-protected aminoepoxide represented by the formula (2) in an aqueous mixture solvent, to obtain crystals of said N-carbamate-protected aminoepoxide having the configuration (2R, 3S) or (2S, 3R).

22. The method according to claim 21, wherein A is benzyl group.

23. The method according to claim 21, wherein R is tert-butyl group.

24. The method according to claim 21, wherein in step (c) said acid is selected from the group consisting of ion exchange resins, acid alumina, acid zeolites, and acid china.

25. The method according to claim 21, wherein in step (d), the aqueous mixture solvent is a mixture solvent of at least one or more organic solvent selected from the group consisting of acetone, methanol, ethanol, 2-propanol and acetonitrile, and water.

26. A method for producing an N-carbamate-protected β-aminoepoxide crystal, comprising:
(d) crystallizing the N-carbamate-protected aminoepoxide represented by the formula (2) in an aqueous mixture solvent:

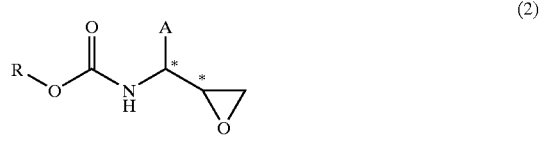
(2)

wherein in formula (2):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone; and
* represents asymmetric carbon atom; and wherein the steric configuration at 2- and 3-positions is (2R, 3S) or (2S, 3R), to obtain crystals of said N-carbamate-protected aminoepoxide having the configuration (2R, 3S) or (2S, 3R).

27. The method according to claim 26, wherein A is benzyl group.

28. The method according to claim 26, wherein R is tert-butyl group.

29. The method according to claim 26, wherein the aqueous mixture solvent is a mixture solvent of at least one organic solvent selected from the group consisting of acetone, methanol, ethanol, 2-propanol and acetonitrile, and water.

30. A method for producing an N-carbamate-protected aminoepoxide comprising the following step (c'):
(c') treating a N-carbamate-protected β-aminoepoxide comprising at least a diastereomer thereof which has the configuration of (2R, 3R) or (2S, 3S) as an impurity and being represented by the formula (2):

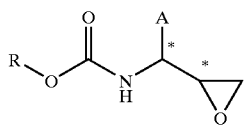

wherein in formula (2):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone; and
* represents asymmetric carbon atom; and wherein the steric configuration at 2- and 3-positions is (2R, 3S) or (2S, 3R); with an acid selected from the group consisting of ion exchange resins, acid alumina, acid zeolites, and acid china, thereby converting the diastereomer to oxazolidin-2-one derivative represented by the formula (3):

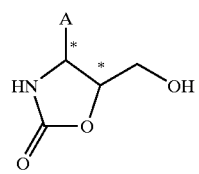

wherein in formula (3), A and * have the same meaning as recited above; and wherein the steric configuration at 4- and 5-positions is (4S, 5R) or (4R, 5S); and separating and removing the resulting oxazolidin-2-one derivative in water or an aqueous mixture solvent.

31. A method for producing an N-carbamate-protected β-aminoepoxide crystal, comprising:
(a) dissolving N-carbamate-protected β-aminoalcohol comprising at least a diastereomer thereof as an impurity and being represented by the formula (1), in at least one solvent selected from the group consisting of aromatic hydrocarbon, aryl halide, cyclohexane, aqueous mixture, acetone and 2-propanol, to remove insoluble material:

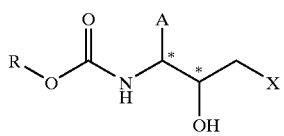

wherein in formula (1):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone;
X represents halogen atom; and
* represents asymmetric carbon atom; and wherein the steric configuration at 2- and 3-positions is (2R, 3S) or (2S, 3R); and
said diastereomer which exists as an impurity has a steric configuration of (2R, 3R) or (2S, 3S);
(b) treating the N-carbamate-protected β-aminoalcohol represented by the formula (1) with a base, thereby converting the N-carbamate-protected β-aminoalcohol to N-carbamate-protected β-aminoepoxide represented by the formula (2):

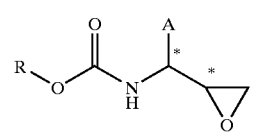

wherein in formula (2), R, A and * have the same meanings as recited above; and wherein the steric configuration at 2- and 3-positions is (2R, 3S) or (2S, 3R) and wherein said N-carbamate-protected β-aminoepoxide represented by formula (2) comprises as an impurity a diastereomer having the configuration of (2R, 3R) or (2S, 3S); and
(d) crystallizing the N-carbamate-protected aminoepoxide represented by the formula (2) in an aqueous mixture solvent, to obtain crystals of said N-carbamate-protected aminoepoxide having the configuration (2R, 3S) or (2S, 3R).

32. The method according to claim 31, wherein A is benzyl group.

33. The method according to claim 31, wherein R is tert-butyl group.

34. The method according to claim 31, wherein in step (a), the aromatic hydrocarbon solvent is at least one selected from the group consisting of toluene, chlorobenzene, xylene and benzene; the aqueous mixture solvent is a mixture solvent of at least one organic solvent selected from the group consisting of methanol, ethanol, 1-propanol, 2propanol, acetone, 2-butanone, acetonitrile and tetrahydrofuran, and water.

35. The method according to claim 31, wherein in step (a), the aromatic hydrocarbon solvent is at least one selected from the group consisting of toluene and xylene; and the aqueous mixture solvent is a mixture solvent of at least one organic solvent selected from the group consisting of methanol, ethanol and 2-propanol, and water.

36. The method according to claim 31, wherein the solvent in step (a) is selected from the group consisting of toluene, xylene and a mixture solvent of 2-propanol and water.

37. The method according to claim 31, wherein in step (c), said acid is selected from the group consisting of ion exchange resins, acid alumina, acid zeolites, and acid china.

38. The method according to claim 31, wherein in step (d), the aqueous mixture solvent is a mixture solvent of at least one organic solvent selected from the group consisting of acetone, methanol, ethanol, 2-propanol and acetonitrile, and water.

39. The method according to claim 1, wherein the content of the diastereomer impurity, based on the total content of the N-carbamate-protected β-aminoalcohol of formula (1) and the diastereomer impurity, produced in step (a), is less than 6% by weight.

40. The method according to claim 9, wherein the content of the diastereomer impurity, based on the total content of the N-carbamate-protected β-aminoalcohol of formula (1) and the diastereomer impurity, produced in step (a), is less than 6% by weight.

41. The method according to claim 15, wherein the content of the diastereomer impurity, based on the total content of the N-carbamate-protected β-aminoalcohol of formula (1) and the diastereomer impurity, produced in step (a), is less than 6% by weight.

42. The method according to claim 31, wherein the content of the diastereomer impurity, based on the total content of the N-carbamate-protected β-aminoalcohol of formula (1) and the diastereomer impurity, produced in step (a), is less than 6% by weight.

43. The method according to claim 6, wherein the solvent in step (a) is an aqueous mixture solvent of 2-propanol and water.

44. The method according to claim 8, wherein the solvent in step (d) is an aqueous mixture solvent of 2-propanol and water.

45. The method according to claim 14, wherein the solvent in step (a) is an aqueous mixture solvent of 2-propanol and water.

46. The method according to claim 20, wherein the solvent in step (a) is an aqueous mixture solvent of 2-propanol and water.

47. The method according to claim 25, wherein the solvent in step (d) is an aqueous mixture solvent of 2-propanol and water.

48. The method according to claim 29, wherein the aqueous mixture solvent is a mixture of 2-propanol and water.

49. The method according to claim 36, wherein the solvent in step (a) is an aqueous mixture solvent of 2-propanol and water.

50. The method according to claim 48, wherein the solvent in step (d) is an aqueous mixture solvent of 2-propanol and water.

51. The method according to claim 1, wherein step (d) is carried out by cooling the aqueous mixture solvent and then adding seed crystals thereto.

52. The method according to claim 21, wherein step (d) is carried out by cooling the aqueous mixture solvent and then adding seed crystals thereto.

53. The method according to claim 26, wherein step (d) is carried out by cooling the aqueous mixture solvent and then adding seed crystals thereto.

54. The method according to claim 31, wherein step (d) is carried out by cooling the aqueous mixture solvent and then adding seed crystals thereto.

55. The method according to claim 21, wherein in step (c) said acid is a solid acid insoluble in reaction solvents at reaction temperature.

56. A method for producing an N-carbamate-protected aminoepoxide comprising the following step (c'):

(c') treating a N-carbamate-protected β-aminoepoxide comprising at least a diastereomer thereof which has the configuration of(2R, 3R) or (2S, 3S) as an impurity and being represented by the formula (2):

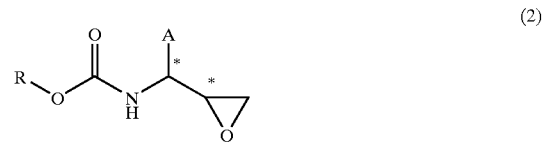

wherein in formula (2):
R represents a lower alkyl group, benzyl group or fluorenylmethyl group;
A represents an unsubstituted or substituted alkyl group with 1 to 10 carbon atoms, an unsubstituted or substituted aryl group with 6 to 15 carbon atoms or an unsubstituted or substituted aralkyl group with 7 to 20 carbon atoms, or a group containing one or more hetero atoms in the carbon backbone; and
* represents asymmetric carbon atom; and wherein the steric configuration at 2- and 3-positions is (2R, 3S) or (2S, 3R); with an acid which is a solid acid insoluble in reaction solvents at reaction temperature, thereby converting the diastereomer to oxazolidin-2-one derivative represented by the formula (3):

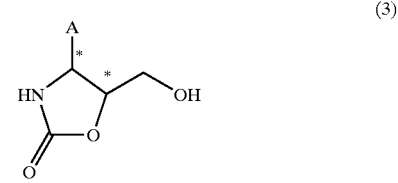

wherein in formula (3), A and * have the same meaning as recited above; and wherein the steric configuration at 4- and 5-positions is (4S, 5R) or (4R, 5S); and separating and removing the resulting oxazolidin-2-one derivative in water or an aqueous mixture solvent.

57. The method according to claim 31, wherein in step (c), said acid is a solid acid insoluble in reaction solvents at reaction temperature.

* * * * *